United States Patent [19]
Oda et al.

[11] Patent Number: 5,131,947
[45] Date of Patent: Jul. 21, 1992

[54] 4-ETHYL-3-(SUBSTITUTED PHENYL)-1-(3-TRIFLUOROMETHYL-PHENYL)-2-PYRROLIDINONE DERIVATIVES, HERBICIDAL COMPOSITIONS CONTAINING THEM AND USE THEREOF

[75] Inventors: Kengo Oda; Koichi Moriyasu; Kiyoshi Arai; Kanji Tomiya; Miura Tohru; Makoto Nishida, all of Kanagawa; Masami Oyamada, Chiba; Akie Fujiwara, Kanagawa, all of Japan

[73] Assignee: Mitsui Toatsu Chemicals Incorporated, Tokyo, Japan

[21] Appl. No.: 494,725

[22] Filed: Mar. 14, 1990

[30] Foreign Application Priority Data

Mar. 15, 1989 [JP] Japan .................................. 1-060695
Dec. 4, 1989 [JP] Japan .................................. 1-313353

[51] Int. Cl.$^5$ .................... A01N 43/36; C07D 207/26
[52] U.S. Cl. .......................................... 71/95; 548/543
[58] Field of Search ............................. 548/543; 71/95

[56] References Cited

U.S. PATENT DOCUMENTS

| 4,087,270 | 5/1978 | Schneider et al. | 71/95 |
| 4,132,713 | 1/1979 | Broadhurst | 260/326.5 |
| 4,210,589 | 7/1980 | Teach | 260/326.5 |
| 4,443,616 | 4/1984 | Hofer | 548/543 |
| 4,960,457 | 10/1990 | Woolard | 548/543 |

FOREIGN PATENT DOCUMENTS 1350582  4/1974  United Kingdom ................. 58/543

Primary Examiner—Patricia L. Morris
Assistant Examiner—Lenora A. Miltenberger
Attorney, Agent, or Firm—Millen, White & Zelano

[57] ABSTRACT

4-Ethyl-3-(phenyl)-1-(3-trifluoromethylphenyl)-2-pyrrolidinones and corresponding compounds bearing a p-substituent on the 1-position phenyl group and/or a substituent on the 3-position phenyl group exhibit selective herbicidal activities against various weeds which cause problems in rice or upland fields, even at extremely low application rates. They can be prepared by reductive dehalogenation of a corresponding α-haloethyl substituted pyrrolidinone or reductive cyclization of a corresponding N-2-butenyl-N-(substituted phenyl)-haloacetyl-3-trifluoromethylaniline.

7 Claims, No Drawings

4-ETHYL-3-(SUBSTITUTED PHENYL)-1-(3-TRIFLUOROMETHYLPHENYL)-2-PYRROLIDINONE DERIVATIVES, HERBICIDAL COMPOSITIONS CONTAINING THEM AND USE THEREOF

BACKGROUND OF THE INVENTION

1. Field of the Invention

The present invention relates to novel 4-ethyl-3-(substituted phenyl)-1-(3-trifluoromethylphenyl)-2-pyrrolidinones, processes for the preparation and use thereof, and herbicidal compositions containing them.

2. Prior Art

Possession of herbicidal activities by certain types of 2-pyrrolidinone derivatives has already been disclosed, for example, in U.S. Pat. No. 4,110,105, U.S. Pat. No. 4,210,589, European Patent Publication No. 134,564A and European Patent Publication No. 55,215A. Further, preparation processes of 2-pyrrolidinone derivatives are disclosed in U.S. Pat. No. 4,132,713.

3-Chloro-4-(chloromethyl)-1-(3-trifluoromethylphenyl)-2-pyrrolidinone (generally called "fluorochloridone") which is a typical example of the compounds disclosed in U.S. Pat. No. 4,110,105 and U.S. Pat. No. 4,210,589, has been available commercially.

Fluorochloridone must be applied at a relatively high rate when employed as a herbicide and the use of this compound in paddy fields at an application rate effective against certain harmful weeds results in serious injury to the rice plants (Oryza sativa) therein.

SUMMARY OF THE INVENTION

An object of the present invention is to provide selective herbicides which in paddy fields and upland fields, do not injure commercial crops therein and moreover are effective against harmful weeds even at low application rates.

The present inventors have proceeded with a further investigation on 2-pyrrolidinone derivatives with a view toward obtaining herbicides which, compared to the conventional herbicides, have excellent effects at lower application rates and do not cause crop injury. As a results, it has been found that novel 4-ethyl-3-(substituted phenyl)-1-(3-trifluoromethylphenyl)-2-pyrrolidinone derivatives. In a composition aspects, this invention relates to novel compounds represented by formula (I) having a specific phenyl group and an ethyl group at the 3- and 4-positions of the pyrrolidinone ring, respectively, are excellent as herbicides and moreover feature no injury to economical crops.

The pyrrolidinone derivatives according to the present invention have the structure represented by formula (I)

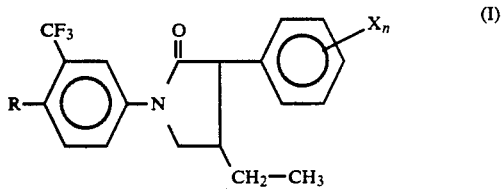

including the 3,4-cis and 3,4-trans stereoisomers thereof, wherein R represents a hydrogen, fluorine or chlorine atom, X a hydrogen, fluorine, chlorine or bromine atom or a trifluoromethyl, methyl, cyano or nitro group, n is 1 or 2, and when n is 2, both Xs may be the same or different.

In another composition aspect, this invention relates to herbicidal compositions comprising a herbicidially effective amount of a compound of formula (I) in admixture with a carrier.

In a method of use aspect, this invention relates to a method of controlling weeds in an area susceptible to infestation by weeds, preferably an agricultural area containing a commercial crop, especially a rice paddy field, which comprises applying thereto a weed controlling amount of a compound of formula (I).

In a first process of making aspect, this invention relates to a process for producing a compound of formula (I) which comprises cyclizing with a trialkyltin hydride an amide derivative represented by the following formula (II):

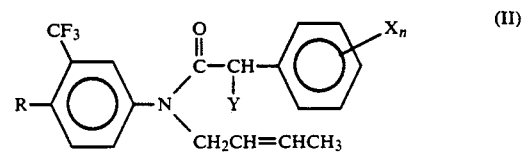

wherein R, X and n have the same meanings as defined above and Y represents a halogen atom.

In a second process of making aspect, this invention relates to a process for preparing a compound of formula (I) which comprises dehalogenating in the presence of a reducing agent a pyrrolidinone derivative represented by the following formula (V):

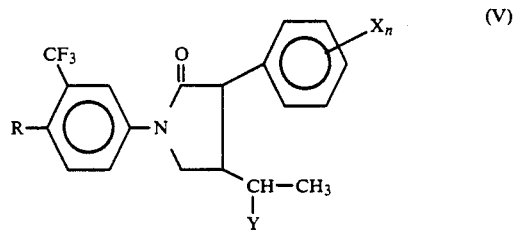

wherein R, X and n have the same meanings as defined above and Y represents a halogen atom.

Herbicidal compositions containing one or more of the compounds of the present invention exhibit marked herbicidal activities at extremely low application rates against various weeds, especially those which cause problems in paddy fields or upland fields, and moreover have a broad herbicidal spectrum. Nevertheless, they show outstanding selectivity to certain types of commercial crops, especially to rice (Oryza sativa) in paddy fields, so that they can be used with extreme safety in agricultural environments.

DETAILED DESCRIPTION OF THE PREFERRED EMBODIMENTS

Illustrative of the pyrrolidinone derivatives according to the present invention represented by formula (I), are those wherein:

(a) the geometric isomerism is 3,4-trans;

(b) X is F, Cl, Br, $CF_3$, $NO_2$ or CN, including those of (a), above;

(c) n is 1 and X is at the 3 position, including those of (a), (b), above;

(d) n is 2 and X is at the 3,4- or 3,5-position, including those of (a), (b), above;

(e) X is F at the 3-position, including those of (a), above;

(f) X is F at the 3-position, R is Cl or F, including those of (a), above.

The compounds of this invention can be in the form of a mixture of the 3,4-cis and 3,4-trans geometric isomers thereof or as one isomer thereof substantially free from the other isomer. The herbicidal compositions of this invention contain one or more of the pyrrolidinone derivatives.

As noted above, fluorochloridine which has heretofore been used requires a relatively high application rate when applied in a field. However, due to the serious injury which it causes to rice (Oryza sativa), its application is extremely limited, especially in paddy fields. In contrast, the compounds according to the present invention can be applied at lower rates to upland crops and moreover, can be used in paddy fields owing to their high safety to rice plants (Oryza sativa). Accordingly, they are applicable to an extremely wide range of commercial crops.

Although the compounds of the present invention have the same structural nucleus as the compounds of the above-described prior art publications, they are different in that the halogen atom at the 3-position and the chloromethyl group at the 4-position of the pyrrolidinone ring have been converted to a specific phenyl group and to an ethyl group, respectively. This conversion has an extremely important effect on herbicidal activity. As a result of this conversion, their activities as herbicides have been enhanced and, in paddy fields, the difference in selectivity between rice plants (Oryza sativa) and weeds has been widened, whereby they can be used more safely in paddy fields.

The herbicidal compositions containing one or more compounds of this invention as active ingredients have, as their characteristic activities, herbicidal activity against most of the harmful weeds which cause problems in paddy fields or upland fields, for example, gramineous weeds such as barnyardgrass (Echinochloa), cyperaceous weeds such as Cyperus microiria and bulrush (Sirpus juncoides), and perennial broadleaf weeds such as Sagittaria pygmaea in paddy fields; and broadleaf weeds such as amaranth (Amaranthus viridis), henbit (Lamium amplexicaule) and chickweed (Stellaria media), and gramineous weeds such as crabgrass (Digicaria adscendes) and wild Oat (Avena farua) in upland fields. Nevertheless, at application rates effective against these weeds they cause no injury to commercial crops such as rice (Oryza sativa), wheat (Triticum), soybean (Glycine max) and cotton (Gossypium indicum). Further, the herbicidal compositions of the compounds according to the present invention are effective when applied by any application methods such as submerged soil application, soil application, soil incorporation or foliar application.

The 4-ethyl-3-(substituted phenyl)-1-(3-trifluoromethylphenyl)-2-pyrrolidinones according to the present invention are novel compounds and can easily be prepared by subjecting an amide derivative represented by the formula (II) to the following reductive cyclization reaction:

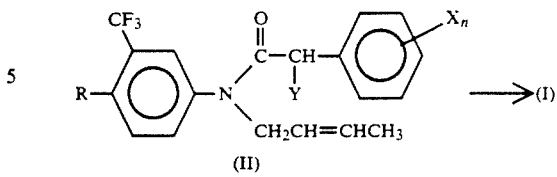

wherein R, X and n have the same meanings as defined above and Y represents a halogen atom.

Exemplary cyclizing agents effective for the above cyclization reaction include alkyltinhydrides, e.g., tributyltin hydride. The reaction is generally conducted in an aromatic solvent, such as benzene, toluene or xylene. The reaction temperature preferably is 50°-140° C., with 60°-90° C. being more preferred. The reaction proceeds by the addition of a catalytic amount of a radical generating agent, such as α,α-azobisisobutyronitrile or benzoyl peroxide, to the reaction mixture. Radiation such as ultraviolet radiation is also effective.

The amide derivative represented by the formula (II) can be prepared by reacting an amine of the formula (III) with a carboxylic acid derivative of the formula (IV):

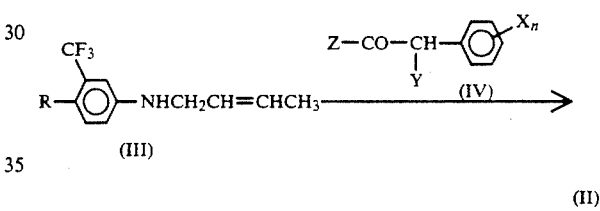

wherein R, X, Y and n have the same meanings as defined above and Z represents a halogen atom.

The reaction is conducted in the absence of a solvent manner or in an inert solvent. Illustrative of suitable inert solvents are aromatic hydrocarbons such as benzene, toluene, xylene, chlorobenzene and dichlorobenzene, halogenated aliphatic hydrocarbons such as dicloromethane, chloroform and carbon tetrachloride, ethers such as diethyl ether, tetrahydrofuran and dioxane, and esters such as ethyl acetate and butyl acetate. In addition, aprotic polar solvents such as dimethylformamide and dimethylsulfoxide are also effective. The reaction proceeds at any desired temperature. It is possible to carry out the reaction in the presence of a base, such as triethylamine, pyridine, N,N-dimethylaniline, sodium hydride, potassium hydride, sodium carbonate, potassium carbonate and sodium bicarbonate.

The amine of the formula (III) can be prepared by the process described in U.S. Pat. No. 4,132,713 or the like. On the other hand, the acid halide of the formula (IV) can be prepared from a corresponding mandelic or phenylacetic acid derivative or the like by a method known per se in the art.

The 4-ethyl-3-(substituted phenyl)-1-(3-trifluoromethylphenyl)-2-pyrrolidinone derivatives according to the present invention can also be prepared by reducibly dehalogenating corresponding 2-pyrrolidinone derivatives represented by the formula (V):

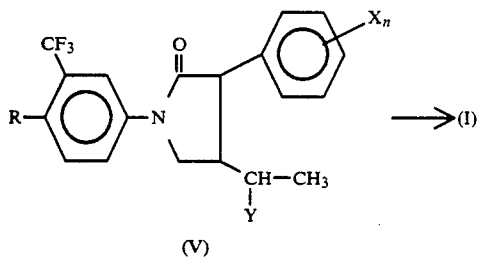

(V)

wherein R, X, Y and n have the same meanings as defined above.

The above reaction is conducted in the presence of a suitable reducing agent in the absence of a solvent or in a solvent. Examples of suitable reducing agents include metals such as iron, zinc, tin and copper and organotin compounds, such as dialkyltin hydrides exemplified by dibutyltin hydride, trialkyltin hydrides typified by tributyltin hydride, diphenyltin hydride and triphenyltin hydride. It is also possible to carry out the reaction using hydrogen in the presence of a hydrogenation catalyst, e.g., palladium-carbon, Raney nickel or platinum. Other reductive means such as electrolytic reduction are also effective in some instances. Suitable exemplary solvents include aromatic hydrocarbons such as benzene, toluene and xylene, ethers such as dioxane, tetrahydrofuran and diethyl ether, esters such as ethyl acetate and butyl acetate, lower alcohols such as methanol, ethanol, propanol and butanol, and lower organic acids such as acetic acid, propionic acid and butyric acid. The reaction temperature may range from 0° C. to 160° C., e.g., the refluxing temperature of the solvent. The reaction time can range from as short as several seconds to 50 hours or longer. It is also possible to conduct the reaction in the presence of a suitable organic acid such as acetic acid or formic acid or an alkali metal salt thereof or a suitable mineral acid such as hydrochloric acid.

The 2-pyrrolidinone derivatives of the formula (V) can be prepared by subjecting a corresponding amide derivative of formula (II) to the following cyclization reaction in the presence of suitable catalyst:

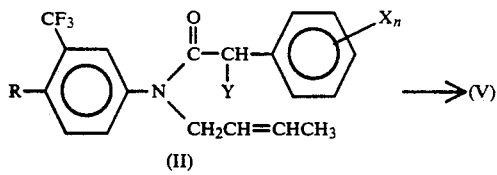

(II)

wherein R, X, Y and n have the same meanings as defined above.

The reaction is generally conducted in a solvent. Preferred solvents are those not impeding the reaction, including diethylene glycol dimethyl ether, dimethylformamide, dimethylacetamide, dimethylsulfoxide, acetonitrile, benzene, toluene and xylene. As a suitable catalyst, a transition metal catalyst, namely, one providing ferrous ions or cuprous ions, are preferred. Specific examples of the transition metal catalyst include ferrous chloride and cuprous chloride. Addition of an amine to the reaction mixture is also extremely effective for accelerating the reaction. The reaction temperature can vary widely, e.g., 20°-190° C., with 70°-140° C. being preferred.

The compounds of the formula (I) according to this invention, which can be obtained as described above, are generally mixed with an inert liquid or solid carrier and then formed into a commonly-used formulation such as powder, granules, wettable powder, emulsion and flowable formulation. One or more auxiliary agents can also be added if desired or necessary for formulation purposes.

Any carrier can be used as long as it is usable in conventional agricultural or horticultural chemicals, no matter whether it is solid or liquid. No particular limitation is therefore imposed on the carrier. Exemplary solid carriers include mineral powders such as clay, talc, bentonite, calcium carbonate, diatomaceous earth and white carbon; vegetable powders such as soybean flour and starch; high molecular compounds such as petroleum resins, polyvinyl alcohol and polyalkylene glycols; urea; and waxes. Illustrative liquid carriers include various organic solvents such as xylene, toluene, methylnaphthalene and alkylbenzenes; and water.

As auxiliary agents, surfactants, binders, stabilizers and the like which are generally used in agricultural or horticultural chemicals can be used either singly or in combination. In some instances, industrial bactericides, antiseptics and the like can also be incorporated for the control of bacteria and fungi.

As exemplary surfactants, non-ionic, anionic, cationic and amphoteric surfactants can be used either singly or in combination. Those obtained by adding ethylene oxide or propylene oxide to alkyl phenols, higher alcohols, alkylnaphthols, higher fatty acids, fatty acid esters and the like can be used as preferred non-ionic surfactants. Exemplary anionic surfactants include the alkylsulfonate salts, alkyl sulfate ester salts, phosphate ester salts and the like of alkylphenols, alkylnaphthols, higher alcohols, higher fatty acids, fatty acid esters and the like. Lignine sulfonate salts and the like are also preferred.

The content of each compound of the formula (I) in the herbicide according to the invention varies widely depending on the formulation and end use. In general, it is 0.01-20 wt. % in a powder, 1-50 wt. % in a wettable powder, 0.01-10 wt. % in a granule, 1-50 wt. % in an emulsion, 1-50 wt. % in a flowable formulation and 1-50 wt. % in a dry flowable formulation. Preferably, it is 0.1-3 wt. % in a powder, 10-40 wt. % in a wettable powder, 0.1-5 wt. % in a granule, 10-30 wt. % in an emulsion, 20≧30 wt. % in a flowable formulation and 20-40 wt. % in a dry flowable formulation.

The herbicides of the invention may be used in combination with one or more other herbicides and/or one or more of bactericies, insecticides, plant growth regulators, fertilizers and soil improving agents. In some instances, certain synergistic effects may be expected from such combined use.

EXAMPLES

Synthesis examples of certain compounds according to the invention will be described by the following examples.

Example 1

Synthesis of 4-ethyl-3-phenyl-1-(3-trifluoromethylphenyl)-2-pyrrolidinone (Compound Nos. 1 & 2)

N-(2-Butenyl)-N-(3-trifluoromethylphenyl)-2-chloro-2-phenylacetamide (1.5 g) was added to 15 ml of benzene, followed by the addition of 1.2 g of tributyltin hydride and an extremely small amount of α,α-azobisisobutyronitrile (AIBN) under stirring at the refluxing temperature. After the reaction mixture was continuously stirred for 70 minutes, 40 ml of saturated saline were added, followed by extraction with toluene. After the extract was dried over anhydrous magnesium sulfate, the extract was concentrated in an evaporator and then subjected to chromatography on a silica gel column. The 3,4-trans isomer (0.67 g) and the 3,4-cis isomer (0.27 g) were obtained.

Example 2

Synthesis of 4-ethyl-3-(4-fluorophenyl)-1-(3-trifluoromethylphenyl)-2-pyrrolidinone (Compound Nos. & 4)

N-(2-Butenyl)-N-(3-trifluoromethylphenyl)-2-bromo-2-(4-fluorophenyl)acetamide (1.9 g) was added to 20 ml of toluene, followed by the addition of 1.2 ml of tributyltin hydride and an extremely small amount of α,α-azobisisobutyronitrile (AIBN) under stirring at 70° C. After the reaction mixture was continuously stirred for 1 hour, 60 ml of 20% hydrochloric acid were added, followed by extraction with toluene. After the extract was dried over anhydrous sodium sulfate, the extract was concentrated in an evaporator and then subjected to chromatography on a silica gel column. The 3,4-trans isomer (0.9 g) and the 3,4-cis isomer (0.27 g) were obtained.

Example 3

Synthesis of 4-ethyl-3-(3,5-difluorophenyl)-1-(3-trifluoromethylphenyl)-2-pyrrolidinone (Compound No. 13)

N-(2-Butenyl)-N-(3-trifluoromethylphenyl)-2-chloro-2-(3,5-difluorophenyl)acetamide (1.6 g) was added to 30 ml of benzene, followed by the addition of 1.1 ml of tributyltin hydride and a catalytic amount of α,α-azobisisobutyronitrile (AIBN) under stirring at the refluxing temperature. The reaction mixture was then stirred for 20 minutes at the refluxing temperature. The reaction mixture was then concentrated in an evaporator. The resultant concentrate was purified by chromatography on a silica gel, whereby 0.75 g of the 3,4-trans isomer of 4-ethyl-3-(3,5-difluorophenyl)-1-(3-trifluoromethylphenyl)-2-pyrrolidinone and 0.14 g of its 3,4-cis isomer were obtained.

Example 4

Synthesis of 4-ethyl-3-(3-chlorophenyl)-1-(3-trifluoromethylphenyl)-2-pyrrolidinone (Compound No. 11)

To 20 ml of HCl-saturated acetic acid, 1.2 g of 3,4-trans-4-(1-bromoethyl)-3-(3-chlorophenyl)-1-(trifluoromethylphenyl)-2-pyrrolidinone and 7.0 g of zinc powder were added. After the resultant mixture was stirred at 90°-110° C. for 5 hours, the insoluble matter was filtered off and the filtrate was extracted with toluene. The extract was dried over anhydrous sodium sulfate and then concentrated in an evaporator Crystals which gradually precipitated in the course of the evaporation were collected, whereby 0.5 g of the title compound (Compound No. 11) was obtained.

Example 5

Synthesis of 4-ethyl-3-(3-cyanophenyl)-1-(3-trifluoromethylphenyl)-2-pyrrolidinone (Compound No. 35)

To 10 ml of 1,3-dimethyl-2-imidazolidinone, 0.7 g of 4-ethyl-3-(3-bromophenyl)-1-(3-trifluoromethylphenyl)-2-pyrrolidinone (Compound No. 25) and 1.2 g of cuprous cyanide were added. After the resultant mixture was stirred at 160° C. for 4 hours, the insoluble matter was filtered off from the reaction mixture and the filtrate was poured into water, followed by extraction with toluene. The extract was dried over anhydrous sodium sulfate, concentrated in an evaporator, and then purified by chromatography on a silica gel column, whereby 0.35 g of the title compound was obtained.

In addition, other pyrrolidinone derivatives of formula (I) according to the present invention were also synthesized in accordance with the procedures of the above examples.

The thus-obtained compounds of the formula (I) according to the present invention and their physical properties are shown in Table 1.

TABLE 1

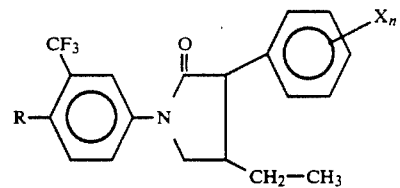

(I)

| Compound No. | R | $X_n$ | Geometric isomerism | Physical properties |
|---|---|---|---|---|
| 1 | H | H | 3,4-trans | NMR(100MHz, CDCl$_3$)δppm: 1.00(3H, t, J=7Hz), 1.50–1.90(2H, m), 2.30–2.80(1H, m), 3.54(1H, d, J=10Hz), 3.61(1H, t, J=8Hz), 4.06(1H, dd, J=8Hz, 9Hz), 7.20–7.75(7H, m), 7.95–8.15(2H, m). IR νneat cm$^{-1}$: 1700 |
| 2 | H | H | 3,4-cis | NMR(100MHz; CDCl$_3$)δppm: 0.96(3H, t, J=7Hz), 1.23–1.74(2H, m), |

TABLE 1-continued

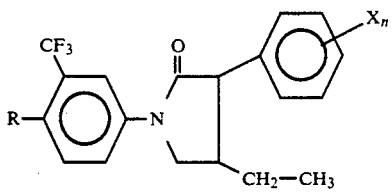
(I)

| Compound No. | Substituents in formula (I) | | Geometric isomerism | Physical properties |
|---|---|---|---|---|
| | R | $X_n$ | | |
| | | | | 2.50–2.85(1H, m), 3.70(1H, dd, J=7Hz, 8Hz), 3.98(1H, d, J=8Hz), 4.04(1H, t, J=7Hz), 7.10–7.60(7H, m), 8.00–8.15(2H, m). IR νneat cm$^{-1}$: 1700. |
| 3 | H | 4-F | 3,4-trans | NMR(100MHz, CDCl$_3$)δppm 1.00(3H, t, J=7Hz), 1.45–1.90(2H, m), 2.20–2.65(1H, m), 3.49(1H, d, J=10Hz), 3.58(1H, t, J=8Hz), 4.03(1H, dd, J=8Hz, 9Hz), 6.96–7.37(4H, m), 7.40–7.60(2H, m), 7.80–8.05(2H, m). IR νnujol cm$^{-1}$: 1700. MP: 82.0–84.0° C. |
| 4 | H | 4-F | 3,4-cis | NMR(100MHz, CDCl$_3$)δppm: 0.95(3H, t, J=7Hz), 1.25–1.75(2H, m), 2.50–2.80(1H, m), 3.67(1H, dd, J=7Hz, 8Hz), 4.02(1H, d, J=9Hz), 4.05(1H, t, J=7Hz), 6.96–7.28(4H, m), 7.36–7.64(2H, m), 7.86–8.05(2H, m). IR νneat cm$^{-1}$: 1700. |
| 5 | H | 3-F | 3,4-trans | NMR(270MHz, CDCl$_3$)δppm: 0.99(3H, t, J=7.6Hz), 1.49–1.60(1H, m), 1.70–1.81(1H, m), 2.41–2.56(1H, m), 3,51(1H, d, J=10.5Hz), 3.60(1H, t, J=9.5Hz), 4.04(1H, dd, J=7.8Hz, 9.5Hz), 6.97–7.07(3H, m), 7.31–7.53(3H, m), 7.93–7.96(2H, m). IR νnujol cm$^{-1}$: 1700. MP: 98.5–100.0° C. |
| 6 | H | 3-F | 3,4-cis | NMR(270MHz, CDCl$_3$)δppm: 0.92(3H, t, J=7.8Hz), 1.22–1.73(2H, m), 2.63–2.74(1H, m), 3.69(1H, dd, J=7.4Hz, 9.3Hz), 4.00(1H, d, J=8.9Hz), 4.03(1H, dd, J=7.3Hz, 9.3Hz), 6.87–7.10(3H, m), 7.25–7.57(3H, m), 7.93–8.04(2H, m). IR νneat cm$^{-1}$: 1700. |
| 7 | H | 4-CF$_3$ | 3,4-trans | NMR(270MHz, CDCl$_3$)δppm: 0.99(3H, t, J=7.5Hz), 1.50–1.66(1H, m), 1.68–1.85(1H, m), 2.45–2.58(1H, m), 3.58(1H, d, J=10.3Hz), 3.63(1H, t, J=9.5Hz), 4.06(1H, dd, J=7.3Hz, 9.5Hz), 7.40(2H, d, J=7.8Hz), 7.44–7.56(2H, m), 7.65(2H, d, J=7.8Hz), 7.87–7.96(2H, m). IR νnujol cm$^{-1}$: 1700. MP: 94.5–96.4° C. |
| 8 | H | 4-CF$_3$ | 3,4-cis | NMR(270MHz, CDCl$_3$) δppm: 0.92(3H, t, J=7.3Hz), 1.18–1.75(2H, m), 2.63–2.78(1H, m), 3.70(1H, dd, J=6.9Hz, 10.0Hz), 4.06(1H, dd, J=8.1Hz, 10.0Hz), 4.08(1H, d, J=8.9Hz), 7.25–7.29(2H, m), 7.42–7.65(4H, m), 7.94–8.04(2H, m). IR νneat cm$^{-1}$: 1700. |
| 9 | H | 3-CF$_3$ | 3,4-trans | NMR(270MHz, CDCl$_3$)δppm: 0.99(3H, t, J=7.3Hz), 1.48–1.62(1H, m), 1.70–1.82(1H, m), 2.43–2.59(1H, m), 3.58(1H, d, J=10.5Hz), 3.63(1H, t, J=9.5Hz), 4.06(1H, dd, J=7.8Hz, 9.5Hz), 7.36–7.60(6H, m), 7.92–7.97(2H, m). IR νnujol cm$^{-1}$: 1700. MP: 87.0–88.5° C. |
| 10 | H | 3-CF$_3$ | 3,4-cis | NMR(270MHz, CDCl$_3$)δppm: 0.89(3H, t, J=7.3Hz), 1.18–1.74(2H, m), 2.63–2.77(1H, m), 3.71(1H, dd, J=6.9Hz, 9.5Hz), 4.05(1H, dd, J=8.0Hz, 10.0Hz), 4.09(1H, d, J=8.4Hz), 7.30–7.65(6H, m), |

TABLE 1-continued

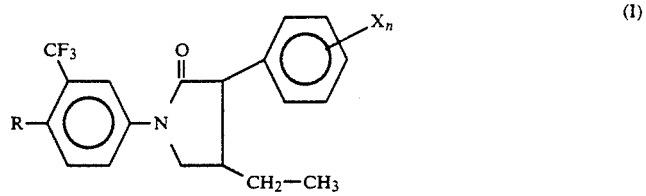
(I)

| Compound No. | Substituents in formula (I) | | Geometric isomerism | Physical properties |
|---|---|---|---|---|
| | R | $X_n$ | | |
| 11 | H | 3-Cl | 3,4-trans | 7.93–8.03(2H, m). IR $\nu$neat cm$^{-1}$: 1705. NMR(270MHz, CDCl$_3$)δppm: 0.99(3H, t, J=7.6Hz), 1.48–1.65(1H, m), 1.70–1.85(1H, m), 2.40–2.55(1H, m), 3.49(1H, d, J=10.3Hz), 3.60(1H, t, J=9.5Hz), 4.03(1H, dd, J=7.6Hz, 9.5Hz), 7.10–7.19(1H, m), 7.25–7.50(5H, m), 7.92–7.97(2H, m). IR $\nu$nujol cm$^{-1}$: 1705. MP: 105.9–106.8° C. |
| 12 | H | 3-Cl | 3,4-cis | NMR(270MHz, CDCl$_3$)δppm: 0.92(3H, t, J=7.3Hz), 1.18–1.74(2H, m), 2.60–2.74(1H, m), 3.69(1H, dd, J=7.2Hz, 9.5Hz), 3.98(1H, d, J=8.9Hz), 4.03(1H, dd, J=7.6Hz, 9.5Hz), 7.02–7.07(1H, m), 7.16(1H, m), 7.26–7.35(2H, m), 7.43–7.56(2H, m), 7.93–8.03(2H, m). IR $\nu$neat cm$^{-1}$: 1700. |
| 13 | H | 3,5-F$_2$ | 3,4-trans | NMR(270MHz, CDCl$_3$)δppm: 0.97(3H, t, J=7.6Hz), 1.50–1.67(1H, m), 1.70–1.85(1H, m), 2.40–2.55(1H, m), 3.50(1H, d, J=10.5Hz), 3.61(1H, t, J=9.5Hz), 4.04(1H, dd, J=7.8Hz, 9.5Hz), 6.73–6.83(3H, m), 7.41–7.54(2H, m), 7.89–7.96(2H, m). IR $\nu$KBr cm$^{-1}$: 1690. MP: 88.2–89.7° C. |
| 14 | H | 3,5-F$_2$ | 3,4-cis | IR $\nu$KBr cm$^{-1}$: 1690. MP: 90.0–95.0° C. |
| 15 | H | 3,4-F$_2$ | 3,4-trans | NMR(270MHz, CDCl$_3$)δppm: 0.96(3H, t, J=7.3Hz), 1.46–1.66(1H, m), 1.70–1.85(1H, m), 2.37–2.49(1H, m), 3.47(1H, d, J=10.8Hz), 3.60(1H, t, J=9.5Hz), 4.03(1H, dd, J=7.8Hz, 9.5Hz), 6.97–7.23(3H, m), 7.41–7.54(2H, m), 7.91–7.95(2H, m). IR $\nu$nujol cm$^{-1}$: 1700. MP: 76.5–80.5° C. |
| 16 | H | 3,4-F$_2$ | 3,4-cis | NMR(270MHz, CDCl$_3$)δppm: 0.95(3H, t, J=7.3Hz), 1.22–1.72(2H, m), 2.60–2.73(1H, m), 3.67(1H, t, J=9.4Hz), 3.98(1H, d, J=8.4Hz), 4.03(1H, dd, J=9.4Hz, 7.4Hz), 6.90–7.20(3H, m), 7.43–7.57(2H, m), 7.92–8.02(2H, m). IR $\nu$neat cm$^{-1}$: 1700. |
| 17 | H | 3-CH$_3$ | 3,4-trans | NMR(270MHz, CDCl$_3$)δppm: 0.95(3H, t, J=7.9Hz), 1.48–1.68(1H, m), 1.70–1.85(1H, m), 2.37(3H, s), 2.41–2.56(1H, m), 3.46(1H, d, J=10.4Hz), 3.58(1H, t, J=8.9Hz), 4.04(1H, dd, J=7.9Hz, 8.9Hz), 7.04–7.13(3H, m), 7.21–7.32(1H, m), 7.42–7.53(2H, m), 7.89–7.99(2H, m). IR $\nu$neat cm$^{-1}$: 1700. |
| 18 | H | 3-CH$_3$ | 3,4-cis | NMR(270MHz, CDCl$_3$)δppm: 0.95(3H, t, J=7.3Hz), 1.20–1.70(2H, m), 2.32(3H, s), 2.58–2.72(1H, m), 3.72(1H, t, J=8.4Hz), 3.94(1H, d, J=8.4Hz), 4.00(1H, dd, J=7.9Hz, 8.4Hz), 6.87–6.93(1H, m), 7.05–7.11(1H, m), 7.15–7.25(2H, m), 7.42–7.58(2H, m), 7.95(1H, broad s), 8.03–8.06(1H, m). IR $\nu$neat cm$^{-1}$: 1700. |
| 19 | H | 2,4-F$_2$ | 3,4-trans | NMR(270MHz, CDCl$_3$)δppm: 0.98(3H, t, J=7.6Hz), 1.51–1.80(2H, m), 2.41–2.53(1H, m), 3.60(1H, t, J=9.2Hz), |

TABLE 1-continued (I)

Structure: N-[4-R-3-(CF$_3$)phenyl]-3-(X$_n$-phenyl)-4-ethyl pyrrolidinone (with C=O)

| Compound No. | R | X$_n$ | Geometric isomerism | Physical properties |
|---|---|---|---|---|
| | | | | 3.71(1H, d, J=10.8Hz), 4.03(1H, dd, J=7.9Hz, 9.2Hz), 6.80–6.92(2H, m), 7.15–7.25(1H, m), 7.38–7.55(2H, m), 7.80–8.00(2H, m). IR νneat cm$^{-1}$: 1690. |
| 20 | H | 2,4-F$_2$ | 3,4-cis | NMR(270MHz, CDCl$_3$)δppm: 0.91(3H, t, J=7.3Hz), 1.20–1.75(2H, m), 2.63–2.75(1H, m), 3.68(1H, t, J=9.4Hz), 4.01(1H, d, J=8.4Hz), 4.03(1H, dd, J=9.4Hz, 7.4Hz), 6.78–6.90(2H, m), 7.14–7.24(1H, m), 7.38–7.56(2H, m), 7.80–8.00(2H, m). IR νneat cm$^{-1}$: 1700. |
| 21 | H | 3,5-Cl$_2$ | 3,4-trans | NMR(270MHz, CDCl$_3$)δppm: 1.00(3H, t, J=7.4Hz), 1.50–1.82(2H, m), 2.43–2.51(1H, m), 3.46(1H, d, J=10.9Hz), 3.60(1H, t, J=8.9Hz), 4.04(1H, t, J=8.9Hz), 7.16(2H, d, J=1.5Hz), 7.29–7.35(1H, m), 7.42–7.54(2H, m), 7.89–7.96(2H, m). IR νneat cm$^{-1}$: 1700. |
| 22 | H | 3,5-Cl$_2$ | 3,4-cis | NMR(270MHz, CDCl$_3$)δppm: 0.92(3H, t, J=7.4Hz), 1.20–1.65(2H, m), 2.60–2.70(1H, m), 3.70(1H, dd, J=6.9Hz, 9.9Hz), 3.97(1H, d, J=8.4Hz), 4.04(1H, dd, J=7.4Hz, 9.9Hz), 7.08(2H, dd, J=1.5Hz), 7.30–7.35(1H, m), 7.44–7.57(2H, m), 7.91–8.02(2H, m). IR νneat cm$^{-1}$: 1700. |
| 23 | H | 2,3-Cl$_2$ | 3,4-trans | NMR(270MHz, CDCl$_3$)δppm: 0.98(3H, t, J=7.4Hz), 1.45–1.80(2H, m), 2.52–2.63(1H, m), 3.64(1H, t, J=8.9Hz), 4.03(1H, d, J=9.5Hz), 4.08(1H, t, J=8.9Hz), 7.14(1H, dd, J=1.5Hz, 7.9Hz), 7.22(1H, dd, J=1.5Hz, 7.9Hz), 7.42–7.46(2H, m), 7.51(1H, t, J=7.9Hz), 7.91–7.98(2H, m). IR νneat cm$^{-1}$: 1700. |
| 24 | H | 2,3-Cl$_2$ | 3,4-cis | NMR(270MHz, CDCl$_3$)δppm: 0.92(2H, t, J=7.4Hz), 1.25–1.70(2H, m), 2.75–2.90(1H, m), 3.68(1H, dd, J=3.9Hz, 9.9Hz), 4.10(1H, dd, J=6.9Hz, 9.9Hz), 4.63(1H, d, J=8.9Hz), 7.21–7.26(2H, m), 7.39–7.57(3H, m), 7.95–8.00(2H, m). IR νneat cm$^{-1}$: 1700. |
| 25 | H | 3-Br | 3,4-trans | NMR(270MHz, CDCl$_3$)δppm: 0.98(3H, t, J=7.4Hz), 1.48–1.85(2H, m), 2.40–2.55(1H, m), 3.47(1H, d, J=10.3Hz), 3.59(1H, t, J=8.9Hz), 4.03(1H, dd, J=8.2Hz, 8.9Hz), 7.12–7.53(6H, m), 7.92–7.97(2H, m). IR νnujol cm$^{-1}$: 1700. MP: 95.2–96.8° C. |
| 26 | H | 3-Br | 3,4-cis | NMR(270MHz, CDCl$_3$)δppm: 0.92(3H, t, J=7.3Hz), 1.20–1.73(2H, m), 2.60–2.74(1H, m), 3.70(1H, t, J=9.2Hz), 3.99(1H, t, J=9.2Hz), 4.00(1H, d, J=8.5Hz), 7.05–7.55(6H, m), 7.93–8.03(2H, m). IR νneat cm$^{-1}$: 1700. |
| 27 | H | 4-Cl | 3,4-trans | NMR(270MHz, CDCl$_3$)δppm: 0.98(3H, t, J=7.3Hz), 1.48–1.82(2H, m), 2.38–2.52(1H, m), 3.48(1H, d, J=10.3Hz), 3.59(1H, t, J=8.9Hz), 4.02(1H, t, J=8.9Hz), 7.15–7.27(3H, m), |

TABLE 1-continued $$\text{(I)}$$

Structure: 4-R-3-CF$_3$-phenyl-N-pyrrolidinone with 3-position bearing phenyl-X$_n$ group and C=O, 4-position bearing CH$_2$-CH$_3$.

| Compound No. | \multicolumn{2}{l}{Substituents in formula (I)} | | Physical properties |
|---|---|---|---|---|
| | R | X$_n$ | Geometric isomerism | |
| | | | | 7.32–7.52(3H, m), 7.88–7.97(2H, m).<br>IR νneat cm$^{-1}$: 1700. |
| 28 | H | 4-Cl | 3,4-cis | NMR(270MHz, CDCl$_3$)δppm:<br>0.93(3H, t, J=7.3Hz), 1.24–1.73(2H, m),<br>2.58–2.72(1H, m),<br>3.67(1H, dd, J=7.5Hz, 9.9Hz),<br>3.98(1H, d, J=8.9Hz),<br>4.02(1H, dd, J=7.5Hz, 9.5Hz),<br>7.07–7.58(6H, m), 7.92–8.03(2H, m).<br>IR νneat cm$^{-1}$: 1700. |
| 29 | H | 3-NO$_2$ | 3,4-trans | NMR(270MHz, CDCl$_3$)δppm:<br>0.97(3H, t, J=7.4Hz), 1.55–1.83(2H, m),<br>2.50–2.65(1H, m), 3.64(1H, d, J=9.2Hz),<br>3.66(1H, t, J=9.2Hz),<br>4.08(1H, dd, J=8.0Hz, 9.2Hz),<br>7.40–7.67(4H, m), 7.90–7.97(2H, m),<br>8.15–8.23(2H, m).<br>IR νneat cm$^{-1}$: 1700. |
| 30 | H | 3-NO$_2$ | 3,4-cis | NMR(270MHz, CDCl$_3$)δppm:<br>0.92(3H, t, J=7.4Hz), 1.23–1.73(2H, m),<br>2.60–2.72(1H, m), 3.69(1H, t, J=7.7Hz),<br>3.95(1H, d, J=8.2Hz), 4.01(1H, t, J=7.7Hz),<br>7.38–7.66(4H, m), 7.89–7.98(2H, m),<br>8.13–8.24(2H, m).<br>IR νneat cm$^{-1}$: 1700. |
| 31 | F | 3-F | 3,4-trans | NMR(270MHz, CDCl$_3$)δppm:<br>0.99(3H, t, J=7.4Hz), 1.49–1.65(1H, m),<br>1.70–1.83(1H, m), 2.43–2.54(1H, m),<br>3.50(1H, d, J=10.4Hz), 3.58(1H, t, J=9.4Hz)<br>4.00(1H, dd, J=7.8Hz, 9.4Hz),<br>6.95–7.08(3H, m), 7.16–7.39(2H, m),<br>7.86–7.97(2H, m)<br>IR νKBr cm$^{-1}$: 1700.<br>MP: 116.6–117.8° C. |
| 32 | F | 3-F | 3,4-cis | NMR(270MHz, CDCl$_3$)δppm:<br>0.92(3H, t, J=7.4Hz), 1.30–1.72(2H, m),<br>2.63–2.74(1H, m),<br>3.66(1H, dd, J=7.4Hz, 9.4Hz),<br>3.96–4.05(2H, m), 6.84–7.03(3H, m),<br>7.21–7.35(2H, m), 7.88–7.91(1H, m),<br>7.99–8.04(1H, m)<br>IR νneat cm$^{-1}$: 1705. |
| 33 | Cl | 3-F | 3,4-trans | NMR(270MHz, CDCl$_3$)δppm:<br>0.96(3H, t, J=7.5Hz), 1.48–1.65(1H, m),<br>1.70–1.85(1H, m), 2.40–2.55(1H, m),<br>3.50(1H, d, J=10.3Hz), 3.57(1H, t, J=9.1Hz),<br>4.01(1H, t, J=9.1Hz), 6.95–7.09(3H, m),<br>7.31–7.39(1H, m), 7.50(1H, d, J=8.9Hz),<br>7.90(1H, dd, J=8.9Hz, 2.4Hz),<br>8.00(1H, d, J=2.4Hz).<br>IR νnujol cm$^{-1}$: 1700.<br>MP: 131.3–133.2° C. |
| 34 | Cl | 3-F | 3,4-cis | NMR(270MHz, CDCl$_3$)δppm:<br>0.92(3H, t, J=7.3Hz), 1.24–1.74(2H, m),<br>2.60–2.74(1H, m),<br>3.66(1H, dd, J=9.3Hz, 7.1Hz),<br>3.99(1H, d, J=8.4Hz),<br>4.00(1H, dd, J=9.3Hz, 7.4Hz),<br>6.84–7.05(3H, m), 7.23–7.35(1H, m),<br>7.52(1H, d, J=8.4Hz), 7.97–8.05(2H, m).<br>IR νneat cm$^{-1}$: 1700. |
| 35 | H | 3-CN | 3,4-trans | NMR(270MHzm CDCl$_3$)δppm:<br>0.99(3H, t, J=7.3Hz), 1.51–1.84(2H, m),<br>2.41–2.57(1H, m), 3.56(1H, d, J=10.3Hz),<br>3.64(1H, t, J=9.5Hz),<br>4.06(1H, dd, J=7.8Hz, 9.5Hz),<br>7.42–7.64(6H, m), 7.85–7.95(2H, m).<br>IR νnujol cm$^{-1}$: 2230, 1700. |

TABLE 1-continued

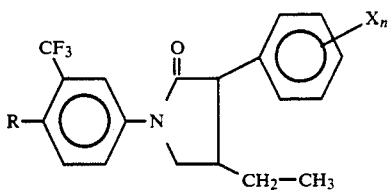

| Compound No. | Substituents in formula (I) | | Geometric isomerism | Physical properties |
|---|---|---|---|---|
| | R | $X_n$ | | |
| | | | | MP: 113.0–115.5° C. |

Further, some synthesis examples of intermediates important for the preparation of the compounds of formula (I) according to the present invention will next be described as referential examples.

Referential Example 1

Synthesis of N-(2-butenyl)-N-(3-trifluoromethylphenyl)-2-bromo-2-(4-fluorophenyl)acetamide In 40 ml of toluene, 2.6 g of 2-bromo-2-(4-fluorophenyl)acetyl chloride were gradually added dropwise at 20°–30° C. under stirring to 2.2 g of N-(2-butenyl)-N-(3-trifluoromethylphenyl)amine. After the reaction mixture was stirred for further 20 minutes, the precipitated insoluble matter was filtered off and 50 ml of toluene were added. The resulting toluene solution was washed twice with a saturated aqueous solution of sodium bicarbonate and twice with saturated saline. The toluene solution was dried over anhydrous sodium sulfate and then concentrated in an evaporator, whereby the intended compound was stoichiometrically obtained in an oily form.

Referential Example 2

Synthesis of N-(2-butenyl)-N-(3-trifluoromethylphenyl)-2-chloro-2-(3,5-difluorophenyl)acetamide Dichloromethane (10 ml) was added with 1.1 g of N-(2-butenyl)-N-(3-trifluoromethylphenyl)amine and then with 1 ml of pyridine. To the resultant mixed solution, 1.3 g of 2-chloro-2- 3,5-difluorophenyl)acetyl chloride were added dropwise under stirring. After the resulting mixture was left over standstill for 2 hours, 40 ml of a saturated aqueous solution of sodium bicarbonate were added. The mixture thus obtained was then extracted with dichloromethane. The organic layer was dried over anhydrous magnesium sulfate and then concentrated in an evaporator, whereby the title compound was stoichiometrically obtained.

In addition, other amide derivatives represented by the formula (II) were also synthesized in accordance with the procedures of Referential Examples 1 and 2.

The thus-obtained amide compounds represented by the formula (II) and their physical properties are shown in Table 2.

TABLE 2

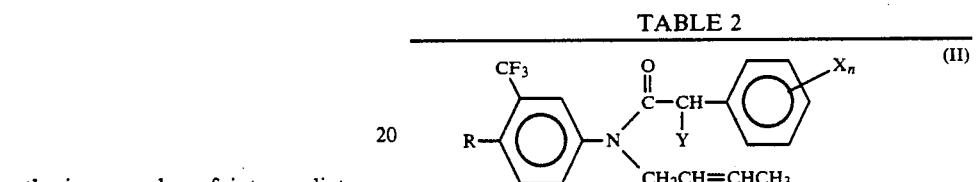

| Substituents in formula (II) | | | |
|---|---|---|---|
| R | $X_n$ | Y | Physical properties |
| H | H | Cl | IR vneat cm$^{-1}$: 1680 n$_D$22.5° C.: 1.4386 |
| H | 4-F | Br | IR vneat cm$^{-1}$: 1680 n$_D$21.2° C.: 1.4292 |
| H | 3-F | Br | IR vneat cm$^{-1}$: 1675 n$_D$30.0° C.: 1.5320 |
| H | 4-CF$_3$ | Br | IR vneat cm$^{-1}$: 1660 n$_D$24.3° C.: 1.5408 |
| H | 3-CF$_3$ | Br | IR vneat cm$^{-1}$: 1680 n$_D$23.4° C.: 1.5089 |
| H | 3-Cl | Br | IR vneat cm$^{-1}$: 1675 n$_D$21.8° C.: 1.5473 |
| H | 3,4-F$_2$ | Cl | IR vneat cm$^{-1}$: 1670 n$_D$19.0° C.: 1.5128 |
| H | 3,5-F$_2$ | Cl | IR vneat cm$^{-1}$: 1665 n$_D$24.8° C.: 1.5092 |
| H | 3-CH$_3$ | Cl | IR vneat cm$^{-1}$: 1675<br>NMR(270MHz, CDCl$_3$)δppm:<br>1.58–1.63(3H, m), 2.30(3H, s),<br>4.12–4.46(2H, m), 5.12(1H, broad s),<br>5.40–5.57(2H, m), 6.95–7.27(6H, m),<br>7.51–7.58(1H, m), 7.64–7.67(1H, m). |
| H | 2,4-F$_2$ | Cl | IR vneat cm$^{-1}$: 1680 n$_D$22.5° C.: 1.5125 |
| H | 3,5-Cl$_2$ | Cl | IR vneat cm$^{-1}$: 1670<br>NMR(270MHz, CDCl$_3$)δppm:<br>1.65(3H, broad s), 4.14–4.42(2H, m),<br>5.04(1H, broad s), 5.43–5.59(2H, m)<br>7.14–7.40(5H, m), 7.55–7.70(1H, m),<br>7.73–7.87(1H, m). |
| H | 3-Br | Cl | IR vneat cm$^{-1}$: 1685 n$_D$23.3° C.: 1.5425 |
| H | 2,3-Cl$_2$ | Cl | IR vneat cm$^{-1}$: 1680<br>NMR(270MHz, CDCl$_3$)δppm:<br>1.64(3H, d, J=3.9Hz), 4.14–4.39(2H, m),<br>5.47–5.50(2H, m), 5.56–5.63(1H, m)<br>7.24–7.32(3H, m), 7.42–7.45(1H, m),<br>7.56(1H, t, J=7.9Hz), 7.67(1H, d, J=8.4hz), 7.74(1H, d, J=7.9Hz). |
| H | 3-NO$_2$ | Br | IR vneat cm$^{-1}$: 1680 n$_D$23.6° C.: 1.5452 |
| H | 4-Cl | Cl | IR vneat cm$^{-1}$: 1675 n$_D$19.8° C.: 1.5417 |
| Cl | 3-F | Br | IR vneat cm$^{-1}$: 1680 n$_D$23.5° C.: 1.5472 |
| F | 3-F | Br | IR vneat cm$^{-1}$: 1675 n$_D$21.8° C.: 1.5305 |

Referential Example 3

Synthesis of N-(2-butenyl)-N-(3-trifluoromethylphenyl)-amine

In 30 ml of dimethylformamide, 1.4 g of anhydrous potassium carbonate and 1.0 g of 1-chloro-2l-butene were added to 1.6 g of 3-aminobenzotrifluoride, followed by stirring for 2 hours from 70° C. to 90° C. After potassium carbonate was filtered off, 100 ml of saturated saline were added and the resulting mixture was extracted with benzene. The extract was dried over anhydrous sodium sulfate, concentrated and then subjected to chromatography on a silica gel column (hexane/ethyl acetate: 35/1, v/v), whereby the intended compound was obtained.

IR $\nu$ neat cm$^{-1}$: 3400.
N$_D$22.8° C.: 1.4903.
Yield: 65.5%.

In a similar manner, the following amine derivatives represented by the formula (III) were also synthesized.

N-(2-Butenyl)-N-(4-chloro-3-trifluoromethylphenyl)amine

IR $\nu$ neat cm$^{-1}$: 3430.
N$_D$22.8° C.: 1.5137.

N-(2-Butenyl)-N-(4-fluoro-3-trifluoromethylphenyl)amine

IR $\nu$ neat cm$^{-1}$: 3400.

| NMR (270 MHz,CDCl$_3$) $\delta$ ppm: | 1.55(1H,broad s), |
|---|---|
| | 1.70–1.74(3H, m), |
| | 3.65–3.76(2H, m), |
| | 5.52–5.58(1H, m), |
| | 5.66–5.77(1H, m), |
| | 6.66–6.75(2H, m), |
| | 6.95–7.03(1H, m). |

Referential Example 4

Synthesis of 2-bromo-2-(4-fluorophenyl)acetyl chloride

Thionyl chloride (14 g) was added to 15.4 g of 4-fluorophenylacetic acid. While the resultant mixture was heated under stirring and reflux, 18 g of bromine were added dropwise. After completion of the dropwise addition, the heating and refluxing was continued for 30 hours. The reaction mixture was cooled and then concentrated in an evaporator, whereby the intended acid chloride was stoichiometrically obtained.

Referential Example 5

Synthesis of 2-chloro-2-(3,5-difluorophenyl)acetyl chloride 3,5-Difluoromandelic acid (2.0 g) and phosphorus pentachloride (4.6 g) were heated under stirring at 160° C. for 30 minutes. The reaction mixture was then concentrated under reduced pressure, whereby the intended acid chloride was stoichiometrically obtained. Other carboxylic acid derivatives represented by the formula (IV) were also synthesized following the procedure of Referential Examples 4 and 5. The thus-obtained carboxylic acids (IV) represented by the formula (IV) and their physical properties are shown in Table 3.

Referential Example 6

Synthesis of 3,5-difluoromandelic acid

Under stirring, 21 ml of a saturated aqueous solution of sodium bisulfite were added little by little to the mixture of 10.0 g of 3,5-difluorobenzaldehyde, 3.6 g of sodium cyanide and 15 ml of water. Upon the gradual addition, ice pieces were added at the same time to maintain the reaction temperature at 20°–30° C. The reaction mixture was stirred for 10 hours and then extracted with benzene. The resulting organic layer was washed with water, dried over anhydrous sodium sulfate and then concentrated under reduced pressure, whereby 10.2 g of crude 3,5-difluoromandelonitrile were obtained.

Concentrated hydrochloric acid (12 ml) was added to the crude product. The resultant mixture was heated under reflux for 60 minutes, added with 30 ml of water and then extracted three times with ethyl acetate (100 ml × 3). The organic layers were combined, washed with saturated saline, dried over anhydrous sodium sulfate, and then concentrated under reduced pressure. The resultant concentrate was crytallized from benzene. The crystals thus formed were collected, washed and then dried, whereby 8.8 g of the intended compound were obtained in a crystalline form (yield: 66.3%). The melting point of the crystals thus obtained was 134.5°–36° C. Other mandelic acid derivatives were also obtained in accordance with the above procedure.

The thus-obtained mandelic acid derivatives and their physical properties are shown in Table 4.

Referential Example 7

Synthesis of 4-(1-bromoethyl)-3-(3-chlorophenyl)-1-(3-trifluoromethylphenyl)-2-pyrrolidinone To 30 ml of toluene, 4.0 g of N-(2-butenyl)-N-(3-trifluoromethylphenyl)-2-bromo-2-(3-chlorophenyl)acetamide and 0.7 g of cuprous chloride were added. The resulting mixture was heated under stirring. When the temperature rose to 90° C., 0.7 ml of di(n-butyl)amine was added, followed by stirring at 90° C.–100° C. Upon an elapsedtime of 15 minutes, the reaction mixture was added to a 20% aqueous solution of hydrochloric acid and then extracted with toluene. The extract was dried over anhydrous magnesium sulfate, concentrated in an evaporator and then subjected to chromatography on a silica gel column (hexane/ethyl acetate: 4/1, v/v), whereby 3.1 g of a compound (a mixture of diastereomers whose steric configurations on the 3- and 4- positions of the pyrrolidinone ring were trans) and 0.4 g of another compound (a mixture of diastereomers whose steric configurations on the 3- and 4-positions of the pyrrolidinone ring were cis) were obtained as first eluate fractions and second eluate fractions, respectively.

Physical properties:
Trans isomer:
IN $\nu$ neat cm$^{-1}$: 1700
n$_D$23.4° C.: 1.5519,
Cis isomer:
IR $\nu$ neat cm$^{-1}$: 1700,
n$_D$20.5° C.: 1.5317,

TABLE 3

$$Z-CO-CH(Y)-\text{C}_6\text{H}_{5-n}X_n \quad (IV)$$

Substituents in formula (IV)

| $X_n$ | Y | Z | Physical properties |
|---|---|---|---|
| 4-F | Br | Cl | NMR(100MHz, CDCl$_3$)$\delta$ppm: 5.64(1H, s), 7.07–7.17(2H, m), 7.41–7.52(2H, m). IR $\nu$neat cm$^{-1}$: 1790 |
| 3-F | Br | Cl | NMR(270MHz, CDCl$_3$)$\delta$ppm: 5.63(1H, s), 7.08–7.17(1H, m), 7.19–7.27(2H, m), 7.36–7.50(1H, m). IR $\nu$neat cm$^{-1}$: 1790 |
| 4-CF$_3$ | Br | Cl | NMR(270MHz, CDCl$_3$)$\delta$ppm: 5.70(1H, s), 7.62(2H, d, J=8.1Hz), 7.70(2H, d, J=8.1Hz). IR $\nu$neat cm$^{-1}$: 1795 |
| 3-CF$_3$ | Br | Cl | NMR(270MHz, CDCl$_3$)$\delta$ppm: 5.69(1H, s), 7.52–7.60(1H, m), 7.64–7.75(3H, m). IR $\nu$neat cm$^{-1}$: 1800 |
| 3-Cl | Br | Cl | NMR(270MHz, CDCl$_3$)$\delta$ppm: 5.61(1H, s), 7.35–7.41(2H, m), 7.48–7.50(1H, m), 7.51–7.59(1H, m). |

TABLE 3-continued

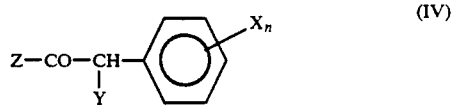

(IV)

Substituents in formula (IV)

| $X_n$ | Y | Z | Physical properties |
|---|---|---|---|
| 3,4-F$_2$ | Cl | Cl | IR νneat cm$^{-1}$: 1790<br>NMR(270MHz, CDCl$_3$)δppm:<br>5.57(1H, s), 7.05-7.40(3H, m). |
| 3-CH$_3$ | Cl | Cl | IR νneat cm$^{-1}$: 1790<br>NMR(270MHz, CDCl$_3$)δppm:<br>2.41(3H, s), 5.59(1H, s), 7.18-7.35(3H, m),<br>7.40-7.51(1H, m). |
| 3-F | Cl | Cl | IR νneat cm$^{-1}$: 1800<br>NMR(270MHz, CDCl$_3$)δppm:<br>5.60(1H, s), 6.95-7.55(4H, m). |
| 3,5-F$_2$ | Cl | Cl | IR νneat cm$^{-1}$: 1800<br>NMR(270MHz, CDCl$_3$)δppm:<br>5.55(1H, s), 6.83-7.10(3H, m). |
| 3-Br | Cl | Cl | IR νneat cm$^{-1}$: 1800<br>NMR(100MHz, CDCl$_3$)δppm:<br>5.57(1H, s), 7.20-7.75(4H, m). |
| 3,5-Cl$_2$ | Cl | Cl | IR νneat cm$^{-1}$: 1800<br>NMR(270MHz, CDCL$_3$)δppm:<br>5.53(1H, s), 7.30-7.55(3H, m). |
| 2,3-Cl$_2$ | Cl | Cl | IR νneat cm$^{-1}$: 1810<br>NMR(270MHz, CDCl$_3$)δppm:<br>6.17(1H, s), 7.33(1H, t, J=7.9Hz),<br>7.46(1H, dd, J=7.9Hz, 1.5Hz),<br>7.56(1H, dd, J=7.9Hz, 1.5Hz). |
| 3-NO$_2$ | Br | Cl | IR νneat cm$^{-1}$: 1810<br>NMR(270MHz, CDCl$_3$)δppm:<br>5.74(1H, s), 7.49-7.70(1H, m), 7.79-7.87(1H, m),<br>8.22-8.40(2H, m). |
| 4-Cl | Cl | Cl | IR νneat cm$^{-1}$: 1800<br>NMR(270MHz, CDCl$_3$)δppm:<br>5.60(1H, s), 7.42(4H, s). |
| 2,4-F$_2$ | Cl | Cl | IR νneat cm$^{-1}$: 1795<br>NMR(270MHz, CDCl$_3$)δppm:<br>6.08(1H, s), 7.05-7.50(3H, m).<br>IR νneat cm$^{-1}$: 1795 |

TABLE 4

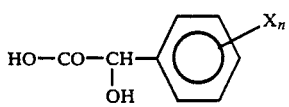

| Substituent on benzene ring $X_n$ | Physical properties |
|---|---|
| 3,4-F$_2$ | IR νnujol cm$^{-1}$: 3430, 1720.<br>MP: 94.0-95.0° C. |
| 2,4-F$_2$ | IR νKBr cm$^{-1}$: 3400, 2960, 1730.<br>MP: 123.5-125.0° C. |
| 3,5-F$_2$ | IR νnujol cm$^{-1}$: 3390, 1710.<br>MP: 134.5-136.0° C. |
| 3-F | IR νKBr cm$^{-1}$: 3430, 2920, 1715.<br>MP: 96.0-97.5° C. |
| 4-Cl | IR νKBr cm$^{-1}$: 3400, 2970, 1725.<br>MP: 117.5-119.0° C. |
| 3,5-Cl$_2$ | NMR(270MHz, d$_6$-acetone)δppm:<br>5.29(1H, s), 7.44(1H, d, J=1.5Hz),<br>7.53(2H, d, J=1.5Hz).<br>MP: 110.6-111.2° C. |
| 3-Br | IR νKBr cm$^{-1}$: 3430, 2920, 1700.<br>MP: 118.0-119.0° C. |
| 3-CH$_3$ | NMR(270MHz, d$_6$-DMSO)δppm:<br>2.30(3H, m), 3.37(1H, broad s),<br>4.96(1H, s)<br>7.07-7.13(1H, m), 7.17-7.25(3H, m).<br>IR νKBr cm$^{-1}$: 3400, 2970, 1730. |
| 2,3-Cl$_2$ | NMR(270MHz, d$_6$-acetone)δppm:<br>5.64(1H, m), 7.33-7.43(1H, m),<br>7.52-7.61(2H, m). |

TABLE 4-continued

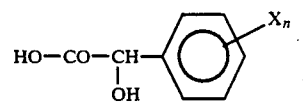

| Substituent on benzene ring $X_n$ | Physical properties |
|---|---|
| | MP: 134.6-135.6° C. |

FORMULATION EXAMPLES AND TESTS

Formulation examples and herbicidal activity tests of certain herbicides according to the present invention will next be described.

Formulation Example 1

(Wettable powder)

A wettable powder was obtained by thoroughly grinding and mixing 20 parts by weight of Compound No. 1 of the invention, 2 parts by weight of "Neopelex" (trade mark, product of Kao Corporation; sodium dodecyl benzene sulfonate), parts by weight of "Neugen EA" (trade name, product of Daiichi Kogyo Seiyaku Industries, Ltd.; polyoxyethylene nonylphenyl ether), 5 parts by weight of white carbon and 71 parts by weight of diatomaceous earth.

Formulation Example 2

(Powder)

A powder was obtained by thoroughly grinding and mixing 1 part by weight of Compound No. 3 of the present invention, 0.5 part by weight of "Emulgen 910" (trade name, product of Kao Corporation; polyoxyethylene nonylphenyl ether) and 98.5 parts by weight of kaolin clay.

Formulation Example 9

(Granule)

One part by weight of Compound No. 5 of the present invention, which had been finely ground, 2 parts by weight of "Neopelex" (trade mark; described above), 2 parts by weight of "Sun Ekisu P252" (trade name product of Sanyo-Kokusaku Pulp Co., Ltd.; sodium lignine sulfonate), 72 parts by weight of bentonite and 23 parts by weight of talc were thoroughly mixed. A suitable amount of water was added to the resultant mixture to wet the same, followed by extrusion of the mass through a small injection molding machine into pellets. After the pellets were dried at 30°-60° C. in air and then crushed into granules, the granules were classified by a sifting machine to collect granules of 0.3-2 mm.

Formulation Example 4

(Emulsion)

An emulsion was obtained by mixing 10 parts by weight of Compound No. 7 of the present invention, 10 parts by weight of "Sorpole 800A" (trade name, product of Toho Chemical Industries Co., Ltd.; a nonionic/anionic surfactant mixture) and 80 parts by weight of o-xylene.

Formulation Example 5

(Flowable formulation)

A flowable formulation was obtained by wet grinding and mixing 30 parts by weight of Compound No. 11 of the present invention and a solution of 10 parts by weight of "Sun Ekisu P252" (trade name, described above) in 50 parts by weight of water and then adding and mixing a solution of 0.2 part by weight of "Kelzan S" (trade name, product of Kelco Corp.; xanthan gum) in 9.6 parts by weight of water and 0.2 part by weight of "Deltop" (trade mark, product of Takeda Chemical Industries, Ltd.; organic iodine fungicide).

Test 1 Treatment of Soil under Submerged Condition

(Pre-emergence Treatment)

1/5000-are Wagner pots were filled with soil. Seeds or tubers of Echinochloa crusgalli bulrush (Scirpus juncoides), Sagittaria pygmaea, monochoria (Monochoria vaginalis) and water nutgrass (Gyperus serotinus) were seeded or planted under submerged condition. Two pairs of rice (Oryza sativa) seedlings (2–3 leaf stage), which had been reared in advance, were transplanted to each pot and were allowed to grow in a green house. Each pair consisted of two rice seedlings. One day later (before emergence of weeds), each pot was treated with a granule which had been prepared by processing a predetermined amount of the test compound in accordance with a similar method to the method described in Formulation Example 3. The state of emergence of weeds and the state of injury of rice were observed 30 days later. The results are summarized in Table 5.

In the table, the degree of damages of each test plant and the degree of injury to rice were determined by comparing the state of growth of the test plant and rice with those of the corresponding plant and rice in untreated pots and are shown in accordance with the following standard:

| Rank | Growth rate (%) expressed in terms of the percentage of dried weight relative to the dried weight of untreated group | |
|---|---|---|
| 5 | 0–5 | (Death) |
| 4 | 6–10 | (Severe damages) |
| 3 | 11–40 | (Medium damages) |
| 2 | 41–70 | (Small damages) |
| 1 | 71–90 | (Slight damages) |
| 0 | 91–100 | (No damages) |

Comparative Compounds A and B represent the following compounds, respectively (this will also apply to Test 2 and Test 3):

A: 1-(3-trifluoromethylphenyl)-3-chloro-4-chloromethyl-2-pyrrolidinone.

B: 1-methyl-3-phenyl-5-(3-trifluoromethylphenyl)-pyridin-4(1H)-one.

In the present test, the herbicide according to the present invention exhibited, compared with Comparative Compounds A and B, higher herbicidal effects against the tested paddy field weeds and excellent safety to rice.

TABLE 5

| Compound No. | Application rate, kg/ha | Echinochloa crusgalli | Monochoria (Monochoria vaginalis) | Bulrush (Scirpus juncoides) | Sagittaria pygmaea | Water nutgrass (Cyperus serotinus) | Rice (Oryza sativa) |
|---|---|---|---|---|---|---|---|
| 1 | 0.1 | 5 | 5 | 4 | 3 | 4 | 0 |
|   | 0.2 | 5 | 5 | 4 | 4 | 5 | 0 |
|   | 0.4 | 5 | 5 | 5 | 5 | 5 | 0 |
| 2 | 0.1 | 3 | 2 | 2 | 2 | 2 | 0 |
|   | 0.2 | 4 | 4 | 3 | 3 | 3 | 0 |
|   | 0.4 | 5 | 5 | 4 | 4 | 4 | 0 |
| 3 | 0.1 | 5 | 5 | 4 | 3 | 4 | 0 |
|   | 0.2 | 5 | 5 | 5 | 4 | 5 | 0 |
|   | 0.4 | 5 | 5 | 5 | 5 | 5 | 0 |
| 4 | 0.1 | 2 | 2 | 2 | 2 | 2 | 0 |
|   | 0.2 | 4 | 3 | 3 | 3 | 3 | 0 |
|   | 0.4 | 5 | 4 | 4 | 4 | 4 | 0 |
| 5 | 0.1 | 5 | 5 | 4 | 3 | 5 | 0 |
|   | 0.2 | 5 | 5 | 5 | 4 | 5 | 0 |
|   | 0.4 | 5 | 5 | 5 | 5 | 5 | 1 |
| 6 | 0.1 | 2 | 2 | 1 | 1 | 2 | 0 |
|   | 0.2 | 4 | 3 | 3 | 2 | 3 | 0 |
|   | 0.4 | 5 | 5 | 4 | 4 | 4 | 0 |
| 7 | 0.1 | 5 | 5 | 3 | 3 | 4 | 0 |
|   | 0.2 | 5 | 5 | 4 | 4 | 5 | 0 |
|   | 0.4 | 5 | 5 | 5 | 5 | 5 | 2 |
| 8 | 0.1 | 3 | 2 | 1 | 2 | 2 | 0 |
|   | 0.2 | 4 | 4 | 3 | 3 | 3 | 0 |
|   | 0.4 | 5 | 5 | 4 | 4 | 4 | 0 |
| 9 | 0.1 | 5 | 5 | 4 | 3 | 3 | 0 |
|   | 0.2 | 5 | 5 | 5 | 4 | 4 | 0 |
|   | 0.4 | 5 | 5 | 5 | 5 | 5 | 0 |
| 10 | 0.1 | 2 | 2 | 2 | 2 | 1 | 0 |
|   | 0.2 | 4 | 3 | 3 | 2 | 3 | 0 |
|   | 0.4 | 5 | 4 | 4 | 4 | 4 | 0 |
| 11 | 0.1 | 5 | 5 | 3 | 4 | 4 | 0 |
|   | 0.2 | 5 | 5 | 4 | 5 | 5 | 0 |
|   | 0.4 | 5 | 5 | 5 | 5 | 5 | 1 |
| 12 | 0.1 | 2 | 2 | 2 | 1 | 2 | 0 |
|   | 0.2 | 4 | 3 | 3 | 2 | 3 | 0 |
|   | 0.4 | 5 | 4 | 4 | 4 | 4 | 0 |
| 13 | 0.1 | 5 | 5 | 4 | 3 | 5 | 0 |
|   | 0.2 | 5 | 5 | 5 | 5 | 5 | 0 |
|   | 0.4 | 5 | 5 | 5 | 5 | 5 | 1 |

TABLE 5-continued

| Compound No. | Application rate, kg/ha | Echinochloa crusgalli | Monochoria (Monochoria vaginalis) | Bulrush (Scirpus juncoides) | Sagittaria pygmaea | Water nutgrass (Cyperus serotinus) | Rice (Oryza sativa) |
|---|---|---|---|---|---|---|---|
| 14 | 0.1 | 1 | 1 | 1 | 1 | 2 | 0 |
|  | 0.2 | 3 | 3 | 3 | 2 | 3 | 0 |
|  | 0.4 | 4 | 5 | 4 | 4 | 4 | 0 |
| 15 | 0.1 | 5 | 5 | 3 | 3 | 4 | 0 |
|  | 0.2 | 5 | 5 | 5 | 4 | 5 | 0 |
|  | 0.4 | 5 | 5 | 5 | 5 | 5 | 1 |
| 16 | 0.1 | 1 | 1 | 1 | 1 | 1 | 0 |
|  | 0.2 | 2 | 3 | 3 | 3 | 3 | 0 |
|  | 0.4 | 5 | 5 | 4 | 4 | 4 | 0 |
| 17 | 0.1 | 5 | 5 | 4 | 3 | 3 | 0 |
|  | 0.2 | 5 | 5 | 5 | 4 | 5 | 0 |
|  | 0.4 | 5 | 5 | 5 | 5 | 5 | 1 |
| 18 | 0.1 | 2 | 2 | 1 | 1 | 2 | 0 |
|  | 0.2 | 4 | 4 | 3 | 3 | 4 | 0 |
|  | 0.4 | 5 | 5 | 4 | 4 | 5 | 0 |
| 19 | 0.1 | 4 | 3 | 2 | 2 | 3 | 0 |
|  | 0.2 | 5 | 4 | 3 | 3 | 4 | 0 |
|  | 0.4 | 5 | 5 | 4 | 4 | 5 | 0 |
| 20 | 0.1 | 2 | 1 | 1 | 1 | 2 | 0 |
|  | 0.2 | 3 | 3 | 2 | 2 | 3 | 0 |
|  | 0.4 | 4 | 4 | 3 | 3 | 4 | 0 |
| 21 | 0.1 | 4 | 3 | 2 | 2 | 3 | 0 |
|  | 0.2 | 5 | 4 | 4 | 3 | 4 | 0 |
|  | 0.4 | 5 | 5 | 4 | 4 | 5 | 0 |
| 22 | 0.1 | 2 | 1 | 1 | 1 | 2 | 0 |
|  | 0.2 | 3 | 3 | 2 | 2 | 3 | 0 |
|  | 0.4 | 5 | 4 | 4 | 4 | 3 | 0 |
| 23 | 0.1 | 4 | 2 | 2 | 3 | 4 | 0 |
|  | 0.2 | 5 | 4 | 4 | 4 | 5 | 0 |
|  | 0.4 | 5 | 5 | 5 | 5 | 5 | 1 |
| 24 | 0.1 | 2 | 1 | 1 | 1 | 2 | 0 |
|  | 0.2 | 3 | 3 | 2 | 3 | 3 | 0 |
|  | 0.4 | 5 | 4 | 4 | 3 | 4 | 0 |
| 25 | 0.1 | 5 | 5 | 4 | 4 | 3 | 0 |
|  | 0.2 | 5 | 5 | 5 | 5 | 5 | 0 |
|  | 0.4 | 5 | 5 | 5 | 5 | 5 | 0 |
| 26 | 0.1 | 2 | 1 | 2 | 2 | 2 | 0 |
|  | 0.2 | 3 | 3 | 3 | 3 | 3 | 0 |
|  | 0.4 | 5 | 4 | 4 | 4 | 4 | 0 |
| 27 | 0.1 | 4 | 3 | 3 | 2 | 3 | 0 |
|  | 0.2 | 5 | 4 | 4 | 3 | 4 | 0 |
|  | 0.4 | 5 | 5 | 5 | 4 | 5 | 0 |
| 28 | 0.1 | 2 | 1 | 1 | 1 | 2 | 0 |
|  | 0.2 | 3 | 3 | 3 | 2 | 4 | 0 |
|  | 0.4 | 5 | 4 | 4 | 4 | 4 | 0 |
| 29 | 0.1 | 5 | 5 | 4 | 3 | 4 | 0 |
|  | 0.2 | 5 | 5 | 5 | 4 | 5 | 0 |
|  | 0.4 | 5 | 5 | 5 | 5 | 5 | 1 |
| 30 | 0.1 | 2 | 2 | 1 | 2 | 2 | 0 |
|  | 0.2 | 3 | 3 | 3 | 3 | 3 | 0 |
|  | 0.4 | 4 | 4 | 4 | 4 | 4 | 0 |
| 31 | 0.1 | 5 | 5 | 4 | 3 | 4 | 0 |
|  | 0.2 | 5 | 5 | 5 | 4 | 5 | 0 |
|  | 0.4 | 5 | 5 | 5 | 5 | 5 | 1 |
| 32 | 0.1 | 2 | 1 | 1 | 1 | 2 | 0 |
|  | 0.2 | 4 | 3 | 3 | 2 | 3 | 0 |
|  | 0.4 | 5 | 4 | 4 | 3 | 4 | 0 |
| 33 | 0.1 | 5 | 4 | 3 | 3 | 3 | 0 |
|  | 0.2 | 5 | 5 | 4 | 4 | 4 | 0 |
|  | 0.4 | 5 | 5 | 5 | 5 | 5 | 1 |
| 34 | 0.1 | 2 | 1 | 1 | 1 | 0 | 0 |
|  | 0.2 | 3 | 2 | 3 | 2 | 2 | 0 |
|  | 0.4 | 4 | 3 | 4 | 3 | 3 | 0 |
| 35 | 0.1 | 5 | 5 | 4 | 4 | 5 | 0 |
|  | 0.2 | 5 | 5 | 5 | 4 | 5 | 0 |
|  | 0.4 | 5 | 5 | 5 | 5 | 5 | 0 |
| A | 0.1 | 2 | 3 | 2 | 1 | 2 | 2 |
|  | 0.2 | 3 | 4 | 3 | 3 | 3 | 3 |
|  | 0.4 | 5 | 5 | 4 | 4 | 5 | 5 |
| B | 0.1 | 3 | 3 | 3 | 3 | 2 | 2 |
|  | 0.2 | 4 | 4 | 4 | 4 | 3 | 4 |
|  | 0.4 | 5 | 5 | 5 | 4 | 4 | 5 |

Comparative Compounds:
A: 1-(3-trifluoromethylphenyl)-3-chloro-4-chloromethyl-2-pyrrolidinone
B: 1-methyl-3-phenyl-5-(3-trifluoromethylphenyl)-pyridin-4(1H)-one

Test 2 Upland Soil Treatment Test

(Pre-emergence Treatment)

Resin-made 1/2500-are pots were filled with the soil of an upland field. Corn (*Zea maize*), wheat (*Triticum*) and soybean (*Glycine max*) were separately seeded. Those seeds were covered with a soil in which seeds of barnyardgrass (Echinochloa), foxtail (*Setaria viridis*), chickweed (*Stellaria media*), shepherdspurse (*Capsella Bursapastoris*), morningglory (*Ipomoea purpurea*) and crabgrass (*Digitaria adscendes*) had been mixed, and were allowed to germinate in a green house. One day later (before emergence of weeds), a wettable powder formulated from a predetermined amount of each test compound in a similar manner to the method described in Formulation Example 1 was diluted with water at predetermined dilution rates and then sprayed at an application rate equal to 10 l per are onto the surface of the soil in each pot by means of a pressure-operated ULV (ultra low volume) sprayer. The state of growth of the weeds and that of injury to the crops were observed and investigated. The results are shown in Table 6, in which the degrees of damages to the respective test plants and the degrees of injury of the crops are shown similarly to Test 1.

In the present test, the compounds according to the present invention showed, compared with Comparative Compounds A and B, higher herbicidal effects against the upland weeds tested and excellent safety to the crops tested, namely, corn, wheat and soybean.

TABLE 6

| Comp'd. No. | Appln. rate, kg/ha | Morning-glory (*Ipomoea purpurea*) | Foxtail (*Setaria viridis*) | Chickweed (*Stellaria media*) | Shepherd-spurse (*Capsella bursapas-toris*) | Barnyard-grass (*Echino-chloa*) | Crabgrass (*Digitaria adscendes*) | Corn (*Zea maize*) | Wheat (*Triticum*) | Soybean (*Glycine max*) |
|---|---|---|---|---|---|---|---|---|---|---|
| 1 | 0.1 | 2 | 3 | 3 | 3 | 3 | 4 | 0 | 0 | 0 |
|  | 0.2 | 3 | 5 | 4 | 4 | 4 | 5 | 0 | 0 | 0 |
|  | 0.4 | 5 | 5 | 5 | 5 | 5 | 5 | 1 | 1 | 0 |
| 2 | 0.1 | 2 | 1 | 2 | 2 | 2 | 2 | 0 | 0 | 0 |
|  | 0.2 | 3 | 3 | 3 | 3 | 3 | 4 | 0 | 0 | 0 |
|  | 0.4 | 5 | 5 | 4 | 4 | 5 | 4 | 0 | 0 | 0 |
| 3 | 0.1 | 3 | 5 | 3 | 4 | 3 | 5 | 0 | 0 | 0 |
|  | 0.2 | 4 | 5 | 5 | 5 | 4 | 5 | 0 | 0 | 0 |
|  | 0.4 | 5 | 5 | 5 | 5 | 5 | 5 | 0 | 1 | 0 |
| 4 | 0.1 | 1 | 1 | 1 | 2 | 2 | 2 | 0 | 0 | 0 |
|  | 0.2 | 3 | 3 | 3 | 3 | 3 | 4 | 0 | 0 | 0 |
|  | 0.4 | 5 | 4 | 4 | 4 | 5 | 4 | 0 | 0 | 0 |
| 5 | 0.1 | 4 | 5 | 5 | 4 | 5 | 5 | 0 | 0 | 0 |
|  | 0.2 | 5 | 5 | 5 | 5 | 5 | 5 | 0 | 0 | 0 |
|  | 0.4 | 5 | 5 | 5 | 5 | 5 | 1 | 1 | 1 | 1 |
| 6 | 0.1 | 2 | 1 | 1 | 1 | 2 | 1 | 0 | 0 | 0 |
|  | 0.2 | 3 | 2 | 2 | 2 | 3 | 3 | 0 | 0 | 0 |
|  | 0.4 | 4 | 4 | 4 | 4 | 5 | 4 | 0 | 0 | 0 |
| 7 | 0.1 | 3 | 4 | 3 | 3 | 3 | 4 | 0 | 0 | 0 |
|  | 0.2 | 4 | 5 | 4 | 4 | 4 | 5 | 0 | 0 | 0 |
|  | 0.4 | 5 | 5 | 5 | 5 | 5 | 5 | 1 | 1 | 0 |
| 8 | 0.1 | 2 | 1 | 2 | 1 | 1 | 2 | 0 | 0 | 0 |
|  | 0.2 | 3 | 3 | 3 | 2 | 3 | 4 | 0 | 0 | 0 |
|  | 0.4 | 5 | 5 | 4 | 4 | 5 | 4 | 0 | 0 | 0 |
| 9 | 0.1 | 3 | 5 | 3 | 5 | 4 | 5 | 0 | 0 | 0 |
|  | 0.2 | 4 | 5 | 5 | 5 | 5 | 5 | 0 | 0 | 0 |
|  | 0.4 | 5 | 5 | 5 | 5 | 5 | 5 | 0 | 1 | 0 |
| 10 | 0.1 | 1 | 1 | 1 | 1 | 1 | 2 | 0 | 0 | 0 |
|  | 0.2 | 2 | 3 | 3 | 2 | 3 | 4 | 0 | 0 | 0 |
|  | 0.4 | 4 | 4 | 4 | 4 | 5 | 4 | 0 | 0 | 0 |
| 11 | 0.1 | 4 | 5 | 5 | 4 | 4 | 4 | 0 | 0 | 0 |
|  | 0.2 | 5 | 5 | 5 | 5 | 5 | 5 | 0 | 0 | 0 |
|  | 0.4 | 5 | 5 | 5 | 5 | 5 | 5 | 1 | 0 | 1 |
| 12 | 0.1 | 2 | 1 | 1 | 1 | 2 | 1 | 0 | 0 | 0 |
|  | 0.2 | 3 | 3 | 3 | 3 | 3 | 3 | 0 | 0 | 0 |
|  | 0.4 | 4 | 4 | 4 | 4 | 5 | 4 | 0 | 0 | 0 |
| 13 | 0.1 | 3 | 5 | 4 | 4 | 4 | 0 | 0 | 0 | 0 |
|  | 0.2 | 4 | 5 | 5 | 5 | 5 | 5 | 0 | 0 | 0 |
|  | 0.4 | 5 | 5 | 5 | 5 | 5 | 5 | 1 | 0 | 1 |
| 14 | 0.1 | 1 | 1 | 1 | 1 | 1 | 1 | 0 | 0 | 0 |
|  | 0.2 | 3 | 2 | 3 | 2 | 3 | 3 | 0 | 0 | 0 |
|  | 0.4 | 4 | 3 | 4 | 3 | 4 | 4 | 0 | 0 | 0 |
| 15 | 0.1 | 3 | 4 | 4 | 4 | 3 | 5 | 0 | 0 | 0 |
|  | 0.2 | 4 | 5 | 5 | 5 | 4 | 5 | 0 | 0 | 0 |
|  | 0.4 | 5 | 5 | 5 | 5 | 5 | 5 | 1 | 0 | 1 |
| 16 | 0.1 | 1 | 1 | 2 | 1 | 1 | 1 | 0 | 0 | 0 |
|  | 0.2 | 2 | 2 | 3 | 2 | 2 | 0 | 0 | 0 | 0 |
|  | 0.4 | 3 | 4 | 4 | 4 | 5 | 4 | 0 | 0 | 0 |
| 17 | 0.1 | 3 | 4 | 3 | 4 | 4 | 5 | 0 | 0 | 0 |
|  | 0.2 | 4 | 5 | 4 | 5 | 5 | 5 | 0 | 0 | 0 |
|  | 0.4 | 5 | 5 | 5 | 5 | 5 | 5 | 0 | 0 | 0 |
| 18 | 0.1 | 1 | 1 | 1 | 1 | 2 | 1 | 0 | 0 | 0 |
|  | 0.2 | 2 | 2 | 3 | 3 | 3 | 2 | 0 | 0 | 0 |
|  | 0.4 | 4 | 4 | 4 | 4 | 4 | 4 | 0 | 0 | 0 |
| 19 | 0.1 | 2 | 3 | 3 | 4 | 3 | 4 | 0 | 0 | 0 |
|  | 0.2 | 3 | 4 | 4 | 4 | 4 | 5 | 0 | 0 | 0 |
|  | 0.4 | 4 | 5 | 5 | 5 | 5 | 5 | 1 | 0 | 0 |
| 20 | 0.1 | 1 | 1 | 1 | 1 | 2 | 2 | 0 | 0 | 0 |

TABLE 6-continued

| Comp'd. No. | Appln. rate, kg/ha | Morning-glory (Ipomoea purpurea) | Foxtail (Setaria viridis) | Chickweed (Stellaria media) | Shepherd-spurse (Capsella bursapas-toris) | Barnyard-grass (Echino-chloa) | Crabgrass (Digitaria adscendes) | Corn (Zea maize) | Wheat (Triticum) | Soybean (Glycine max) |
|---|---|---|---|---|---|---|---|---|---|---|
|    | 0.2 | 2 | 2 | 2 | 2 | 3 | 4 | 0 | 0 | 0 |
|    | 0.4 | 3 | 3 | 3 | 3 | 4 | 4 | 0 | 0 | 0 |
| 21 | 0.1 | 2 | 2 | 3 | 4 | 3 | 4 | 0 | 0 | 0 |
|    | 0.2 | 3 | 3 | 4 | 4 | 4 | 5 | 0 | 0 | 0 |
|    | 0.4 | 4 | 5 | 5 | 5 | 5 | 5 | 0 | 1 | 0 |
| 22 | 0.1 | 0 | 1 | 1 | 1 | 1 | 2 | 0 | 0 | 0 |
|    | 0.2 | 2 | 3 | 3 | 2 | 3 | 4 | 0 | 0 | 0 |
|    | 0.4 | 3 | 4 | 4 | 3 | 4 | 4 | 0 | 0 | 0 |
| 23 | 0.1 | 2 | 2 | 2 | 3 | 2 | 3 | 0 | 0 | 0 |
|    | 0.2 | 3 | 3 | 3 | 4 | 3 | 4 | 0 | 0 | 0 |
|    | 0.4 | 4 | 4 | 4 | 5 | 5 | 4 | 0 | 0 | 1 |
| 24 | 0.1 | 0 | 0 | 1 | 1 | 1 | 1 | 0 | 0 | 0 |
|    | 0.2 | 1 | 1 | 2 | 3 | 3 | 3 | 0 | 0 | 0 |
|    | 0.4 | 2 | 2 | 3 | 4 | 4 | 4 | 0 | 0 | 0 |
| 25 | 0.1 | 3 | 5 | 3 | 5 | 4 | 5 | 0 | 0 | 0 |
|    | 0.2 | 4 | 5 | 4 | 4 | 4 | 5 | 0 | 0 | 0 |
|    | 0.4 | 5 | 5 | 5 | 5 | 5 | 5 | 0 | 1 | 0 |
| 26 | 0.1 | 1 | 1 | 1 | 2 | 2 | 1 | 0 | 0 | 0 |
|    | 0.2 | 3 | 3 | 3 | 2 | 3 | 4 | 1 | 1 | 0 |
|    | 0.4 | 4 | 4 | 4 | 3 | 4 | 4 | 0 | 0 | 0 |
| 27 | 0.1 | 2 | 2 | 2 | 3 | 3 | 3 | 0 | 0 | 0 |
|    | 0.2 | 3 | 3 | 3 | 4 | 4 | 3 | 0 | 0 | 0 |
|    | 0.4 | 4 | 4 | 4 | 5 | 5 | 5 | 0 | 1 | 0 |
| 28 | 0.1 | 0 | 0 | 1 | 1 | 1 | 2 | 0 | 0 | 0 |
|    | 0.2 | 2 | 2 | 2 | 2 | 3 | 3 | 0 | 0 | 0 |
|    | 0.4 | 3 | 3 | 3 | 4 | 5 | 4 | 0 | 0 | 0 |
| 29 | 0.1 | 4 | 4 | 5 | 4 | 5 | 4 | 0 | 0 | 0 |
|    | 0.2 | 5 | 5 | 5 | 5 | 5 | 5 | 0 | 0 | 0 |
|    | 0.4 | 5 | 5 | 5 | 5 | 5 | 5 | 1 | 0 | 1 |
| 30 | 0.1 | 1 | 1 | 1 | 1 | 2 | 1 | 0 | 0 | 0 |
|    | 0.2 | 3 | 2 | 2 | 2 | 3 | 3 | 0 | 0 | 0 |
|    | 0.4 | 4 | 3 | 4 | 3 | 4 | 4 | 0 | 0 | 1 |
| 31 | 0.1 | 2 | 3 | 3 | 4 | 4 | 4 | 0 | 0 | 0 |
|    | 0.2 | 4 | 4 | 4 | 5 | 5 | 5 | 0 | 0 | 0 |
|    | 0.4 | 5 | 5 | 5 | 5 | 5 | 5 | 1 | 0 | 0 |
| 32 | 0.1 | 1 | 1 | 2 | 1 | 1 | 1 | 0 | 0 | 0 |
|    | 0.2 | 2 | 2 | 3 | 2 | 2 | 4 | 0 | 0 | 0 |
|    | 0.4 | 3 | 3 | 4 | 3 | 4 | 4 | 0 | 0 | 0 |
| 33 | 0.1 | 2 | 2 | 2 | 3 | 4 | 3 | 0 | 0 | 0 |
|    | 0.2 | 3 | 4 | 3 | 4 | 5 | 4 | 0 | 0 | 0 |
|    | 0.4 | 4 | 4 | 4 | 5 | 5 | 5 | 0 | 1 | 0 |
| 34 | 0.1 | 0 | 0 | 0 | 1 | 1 | 1 | 0 | 0 | 0 |
|    | 0.2 | 1 | 2 | 1 | 2 | 2 | 2 | 0 | 0 | 0 |
|    | 0.4 | 2 | 3 | 2 | 3 | 4 | 3 | 0 | 0 | 0 |
| 35 | 0.1 | 4 | 5 | 5 | 4 | 5 | 4 | 0 | 0 | 0 |
|    | 0.2 | 5 | 5 | 5 | 5 | 5 | 5 | 0 | 1 | 0 |
|    | 0.4 | 5 | 5 | 5 | 5 | 5 | 5 | 1 | 1 | 1 |
| A  | 0.1 | 0 | 1 | 0 | 1 | 0 | 2 | 0 | 0 | 1 |
|    | 0.2 | 2 | 2 | 2 | 2 | 2 | 4 | 2 | 2 | 1 |
|    | 0.4 | 3 | 4 | 4 | 4 | 4 | 5 | 2 | 2 | 2 |
| B  | 0.1 | 2 | 2 | 1 | 1 | 2 | 2 | 0 | 0 | 0 |
|    | 0.2 | 3 | 3 | 3 | 3 | 3 | 3 | 1 | 1 | 1 |
|    | 0.4 | 4 | 4 | 4 | 4 | 5 | 4 | 2 | 2 | 3 |

Comparative Compounds:
A: 1-(3-trifluoromethylphenyl)-3-chloro-4-chloromethyl-2-pyrrolidinone
B: 1-methyl-3-phenyl-5-(3-trifluoromethylphenyl)-pyridin-4(1H)-one Test 3
Upland Foliar on Test Resin-made 1/10000-are pots were filled with the soil of an upland field. Morningglory (Ipomoea purpurea), smartweed (Polygonum lapathiofolium), hickweed (Stellaria media), lambsquarter (Chenopodium album), barnyardgrass, crabgrass grass (Digitaria adscendes), corn (Zea maize), wheat (Triricum) were separately seeded and were then allowed to germinate in a green house. When each plant grew to the stage of 2-3 leaves, each emulsion formulated in a similar manner to Formulation Example 4 was diluted with water and then sprayed evenly at an application rate equal to 5 l per are (100 m²) by means of a pressure-operated ULV (ultra low volume) sprayer. Upon an elapsed time of 30 days after the spraying of the herbicide, the state of growth of the weeds and that of injury to the crops were observed and investigated. The results are shown in Table 7, in which the degrees of damages to the respective test plants and the degrees of injury of the crops are shown similarly to Test 1.

In the present test, the compounds according to the present invention showed, compared with Comparative Compounds A and B, higher herbicidal effects against the upland weeds tested and excellent safety to the crops tested, namely, corn, wheat and soybean.

TABLE 7

| Comp'd. No. | Appln. rate, kg/ha | Morning-glory (Ipomoea purpurea) | Smartweed (Polygonum lapathifolium) | Chickweed (Stellaria media) | Lambs-quarter (Chenopodium album) | Barnyard-grass (Echinochloa crusgalli) | Crabgrass (Digitaria adscendes) | Corn (Zea maize) | Wheat (Triticum) |
|---|---|---|---|---|---|---|---|---|---|
| 1 | 0.2 | 4 | 4 | 3 | 5 | 4 | 4 | 0 | 0 |
|   | 0.4 | 5 | 5 | 4 | 5 | 5 | 5 | 0 | 0 |
|   | 0.8 | 5 | 5 | 5 | 5 | 5 | 5 | 1 | 1 |
| 2 | 0.2 | 1 | 2 | 2 | 2 | 2 | 3 | 0 | 0 |
|   | 0.4 | 3 | 3 | 3 | 3 | 3 | 4 | 0 | 0 |
|   | 0.8 | 4 | 5 | 4 | 4 | 4 | 5 | 0 | 0 |
| 3 | 0.2 | 5 | 4 | 5 | 5 | 4 | 3 | 0 | 0 |
|   | 0.4 | 5 | 5 | 5 | 5 | 5 | 4 | 0 | 1 |
|   | 0.8 | 5 | 5 | 5 | 5 | 5 | 5 | 0 | 1 |
| 4 | 0.2 | 1 | 1 | 2 | 1 | 1 | 2 | 0 | 0 |
|   | 0.4 | 3 | 3 | 3 | 2 | 2 | 3 | 0 | 0 |
|   | 0.8 | 4 | 4 | 4 | 4 | 4 | 4 | 0 | 0 |
| 5 | 0.2 | 5 | 5 | 5 | 4 | 5 | 5 | 0 | 0 |
|   | 0.4 | 5 | 5 | 5 | 5 | 5 | 5 | 1 | 1 |
|   | 0.8 | 5 | 5 | 5 | 5 | 5 | 5 | 1 | 1 |
| 6 | 0.2 | 1 | 1 | 1 | 1 | 1 | 1 | 0 | 0 |
|   | 0.4 | 2 | 2 | 3 | 2 | 2 | 3 | 0 | 0 |
|   | 0.8 | 4 | 4 | 4 | 4 | 4 | 4 | 0 | 0 |
| 7 | 0.2 | 5 | 4 | 4 | 5 | 4 | 5 | 0 | 0 |
|   | 0.4 | 5 | 5 | 5 | 5 | 5 | 5 | 0 | 0 |
|   | 0.8 | 5 | 5 | 5 | 5 | 5 | 5 | 1 | 1 |
| 8 | 0.2 | 1 | 1 | 1 | 2 | 1 | 2 | 0 | 0 |
|   | 0.4 | 3 | 3 | 2 | 3 | 3 | 3 | 0 | 0 |
|   | 0.8 | 4 | 5 | 4 | 4 | 4 | 5 | 0 | 0 |
| 9 | 0.2 | 5 | 4 | 5 | 5 | 4 | 4 | 0 | 0 |
|   | 0.4 | 5 | 5 | 5 | 5 | 5 | 5 | 0 | 0 |
|   | 0.8 | 5 | 5 | 5 | 5 | 5 | 5 | 0 | 1 |
| 10 | 0.2 | 1 | 2 | 2 | 1 | 1 | 2 | 0 | 0 |
|   | 0.4 | 3 | 3 | 4 | 2 | 2 | 3 | 0 | 0 |
|   | 0.8 | 4 | 4 | 5 | 4 | 4 | 4 | 0 | 0 |
| 11 | 0.2 | 5 | 5 | 4 | 4 | 4 | 5 | 0 | 0 |
|   | 0.4 | 5 | 5 | 5 | 5 | 5 | 5 | 0 | 0 |
|   | 0.8 | 5 | 5 | 5 | 5 | 5 | 5 | 1 | 1 |
| 12 | 0.2 | 1 | 1 | 1 | 1 | 1 | 1 | 0 | 0 |
|   | 0.4 | 3 | 2 | 3 | 2 | 3 | 3 | 0 | 0 |
|   | 0.8 | 4 | 4 | 4 | 4 | 4 | 4 | 0 | 0 |
| 13 | 0.2 | 4 | 5 | 4 | 4 | 5 | 5 | 0 | 0 |
|   | 0.4 | 5 | 5 | 5 | 5 | 5 | 5 | 0 | 0 |
|   | 0.8 | 5 | 5 | 5 | 5 | 5 | 5 | 0 | 1 |
| 14 | 0.2 | 0 | 1 | 0 | 1 | 1 | 1 | 0 | 0 |
|   | 0.4 | 1 | 2 | 2 | 2 | 2 | 3 | 0 | 0 |
|   | 0.8 | 3 | 3 | 4 | 4 | 4 | 5 | 0 | 0 |
| 15 | 0.2 | 4 | 5 | 5 | 4 | 5 | 4 | 0 | 0 |
|   | 0.4 | 5 | 5 | 5 | 5 | 5 | 5 | 0 | 0 |
|   | 0.8 | 5 | 5 | 5 | 5 | 5 | 5 | 1 | 1 |
| 16 | 0.2 | 0 | 1 | 0 | 1 | 1 | 2 | 0 | 0 |
|   | 0.4 | 2 | 2 | 3 | 2 | 3 | 3 | 0 | 0 |
|   | 0.8 | 3 | 4 | 5 | 3 | 4 | 4 | 0 | 0 |
| 17 | 0.2 | 4 | 4 | 5 | 4 | 4 | 5 | 0 | 0 |
|   | 0.4 | 5 | 5 | 5 | 5 | 5 | 5 | 0 | 0 |
|   | 0.8 | 5 | 5 | 5 | 5 | 5 | 5 | 0 | 0 |
| 18 | 0.2 | 0 | 1 | 1 | 2 | 1 | 2 | 0 | 0 |
|   | 0.4 | 2 | 2 | 3 | 3 | 2 | 3 | 0 | 0 |
|   | 0.8 | 3 | 3 | 4 | 4 | 3 | 4 | 0 | 0 |
| 19 | 0.2 | 2 | 3 | 3 | 3 | 3 | 4 | 0 | 0 |
|   | 0.4 | 3 | 4 | 4 | 4 | 5 | 5 | 0 | 0 |
|   | 0.8 | 4 | 5 | 5 | 5 | 5 | 5 | 1 | 1 |
| 20 | 0.2 | 0 | 0 | 1 | 1 | 1 | 2 | 0 | 0 |
|   | 0.4 | 1 | 1 | 2 | 2 | 3 | 3 | 0 | 0 |
|   | 0.8 | 3 | 3 | 4 | 3 | 4 | 5 | 0 | 0 |
| 21 | 0.2 | 2 | 2 | 3 | 3 | 3 | 2 | 0 | 0 |
|   | 0.4 | 3 | 3 | 4 | 4 | 4 | 3 | 0 | 0 |
|   | 0.8 | 4 | 4 | 5 | 5 | 5 | 4 | 0 | 1 |
| 22 | 0.2 | 0 | 1 | 1 | 1 | 1 | 2 | 0 | 0 |
|   | 0.4 | 1 | 2 | 2 | 3 | 2 | 3 | 0 | 0 |
|   | 0.8 | 2 | 3 | 3 | 4 | 3 | 4 | 0 | 0 |
| 23 | 0.2 | 2 | 3 | 2 | 2 | 2 | 3 | 0 | 0 |
|   | 0.4 | 3 | 4 | 3 | 3 | 3 | 3 | 0 | 0 |
|   | 0.8 | 4 | 5 | 4 | 4 | 4 | 4 | 0 | 0 |
| 24 | 0.2 | 0 | 0 | 1 | 1 | 1 | 1 | 0 | 0 |
|   | 0.4 | 1 | 1 | 2 | 2 | 3 | 3 | 0 | 0 |
|   | 0.8 | 2 | 2 | 3 | 3 | 4 | 4 | 0 | 0 |
| 25 | 0.2 | 3 | 4 | 4 | 5 | 5 | 5 | 0 | 0 |
|   | 0.4 | 4 | 5 | 5 | 5 | 5 | 5 | 0 | 0 |
|   | 0.8 | 4 | 5 | 5 | 5 | 5 | 5 | 0 | 0 |
| 26 | 0.2 | 0 | 1 | 1 | 1 | 1 | 2 | 0 | 0 |
|   | 0.4 | 2 | 2 | 2 | 2 | 3 | 3 | 0 | 0 |
|   | 0.8 | 3 | 3 | 4 | 4 | 5 | 5 | 0 | 0 |

TABLE 7-continued

| Comp'd. No. | Appln. rate, kg/ha | Morning-glory (Ipomoea purpurea) | Smartweed (Polygonum lapathifolium) | Chickweed (Stellaria media) | Lambs-quarter (Chenopodium album) | Barnyard-grass (Echinochloa crusgalli) | Crabgrass (Digitaria adscendes) | Corn (Zea maize) | Wheat (Triticum) |
|---|---|---|---|---|---|---|---|---|---|
| 27 | 0.2 | 2 | 3 | 2 | 3 | 3 | 2 | 0 | 0 |
|    | 0.4 | 3 | 3 | 3 | 4 | 4 | 3 | 0 | 0 |
|    | 0.8 | 4 | 4 | 4 | 5 | 5 | 4 | 0 | 0 |
| 28 | 0.2 | 0 | 0 | 0 | 1 | 1 | 2 | 0 | 0 |
|    | 0.4 | 1 | 2 | 1 | 2 | 2 | 3 | 0 | 0 |
|    | 0.8 | 3 | 4 | 4 | 4 | 5 | 4 | 0 | 0 |
| 29 | 0.2 | 4 | 5 | 5 | 4 | 5 | 5 | 0 | 0 |
|    | 0.4 | 5 | 5 | 5 | 5 | 5 | 5 | 0 | 0 |
|    | 0.8 | 5 | 5 | 5 | 5 | 5 | 5 | 0 | 1 |
| 30 | 0.2 | 0 | 0 | 2 | 1 | 1 | 1 | 0 | 0 |
|    | 0.4 | 2 | 2 | 3 | 2 | 2 | 2 | 0 | 0 |
|    | 0.8 | 3 | 4 | 4 | 3 | 4 | 4 | 0 | 0 |
| 31 | 0.2 | 5 | 4 | 4 | 5 | 4 | 4 | 0 | 0 |
|    | 0.4 | 5 | 5 | 5 | 5 | 5 | 5 | 0 | 0 |
|    | 0.8 | 5 | 5 | 5 | 5 | 5 | 5 | 0 | 1 |
| 32 | 0.2 | 0 | 1 | 1 | 2 | 1 | 2 | 0 | 0 |
|    | 0.4 | 2 | 3 | 2 | 3 | 2 | 3 | 0 | 0 |
|    | 0.8 | 3 | 4 | 3 | 4 | 3 | 4 | 0 | 0 |
| 33 | 0.2 | 3 | 4 | 3 | 3 | 4 | 4 | 0 | 0 |
|    | 0.4 | 4 | 5 | 4 | 4 | 5 | 5 | 0 | 0 |
|    | 0.8 | 5 | 5 | 5 | 5 | 5 | 5 | 0 | 0 |
| 34 | 0.2 | 0 | 0 | 1 | 2 | 2 | 2 | 0 | 0 |
|    | 0.4 | 1 | 1 | 2 | 3 | 3 | 3 | 0 | 0 |
|    | 0.8 | 4 | 3 | 3 | 4 | 4 | 3 | 0 | 0 |
| 35 | 0.2 | 4 | 5 | 5 | 5 | 5 | 4 | 0 | 0 |
|    | 0.4 | 5 | 5 | 5 | 5 | 5 | 5 | 0 | 0 |
|    | 0.8 | 5 | 5 | 5 | 5 | 5 | 5 | 1 | 1 |
| A  | 0.2 | 0 | 3 | 1 | 3 | 1 | 2 | 1 | 1 |
|    | 0.4 | 2 | 4 | 3 | 4 | 2 | 3 | 2 | 2 |
|    | 0.8 | 4 | 5 | 5 | 5 | 4 | 5 | 3 | 4 |
| B  | 0.2 | 1 | 2 | 2 | 1 | 1 | 1 | 1 | 1 |
|    | 0.4 | 3 | 3 | 3 | 2 | 3 | 2 | 2 | 2 |
|    | 0.8 | 4 | 4 | 4 | 4 | 4 | 4 | 3 | 3 |

Comparative Compounds:
A: 1-(3-trifluoromethylphenyl)-3-chloro-4-chloromethyl-2-pyrrolidinone
B: 1-methyl-3-phenyl-5-(3-trifluoromethylphenyl)-pyridin-4(1H)-one

We claim:

1. A 3,4-trans-4-ethyl-3-(substituted phenyl)-1-(3-trifluoromethylphenyl)-2-pyrrolidinone of the formula

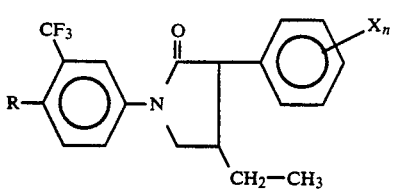

(I)

wherein R represents a hydrogen, fluorine or chlorine atom, X represents a fluorine atom n is 1 or 2; when n is 1, X is at the 3-position of the phenyl group; and when n is 2, the X groups are at 3- and 4-positions or 3- and 5-positions of the phenyl group.

2. A compound of claim 1 wherein X is F at the 3-position, R is Cl or F, as the 3,4-trans isomer.

3. A herbicidal composition comprising an admixture with a carrier as a herbicidally active ingredient a 3,4 trans-4 ethyl-3-(substituted phenyl-1-(3-trifluoromethylphenyl)-2-pyrrolidinone of the formula:

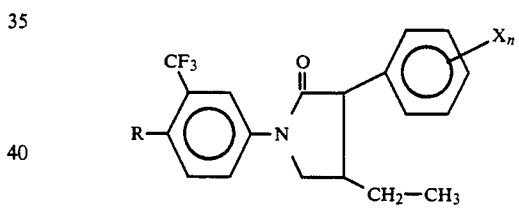

wherein R represents a hydrogen, fluorine or chlorine atom; X represents a fluorine, atom n is 1 or 2; and when n is 1, X is at the 3-position of the phenyl group; and when n is 2, the X groups are at 3- and 4-positions or 3- and 5-positions of the phenyl group.

4. A method of controlling weeds which comprises applying to an area susceptible to infestation with weeds a herbicidally effective amount of a 3,4 trans-4 ethyl-pyrrolidinone of the formula:

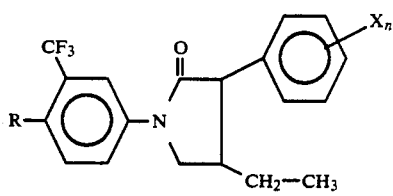

wherein R represents a hydrogen, fluorine or chlorine atoms, X represents a fluorine, n is 1 or 2; and when n is 1, X is at the 3- position of the phenyl group; and when n is 2, the X groups are at 3- and 4- positions or 3- and 5-positions of the phenyl group.

5. A method according to claim 4 wherein the area is a rice paddy.

6. A method according to claim 4 wherein X is 3-F, R is Cl or F, as 3,4-trans isomer.

7. A method according to claim 5 wherein X is 3-F, R is Cl or F, as 3,4-trans isomer.

* * * * *